US006146627A

United States Patent [19]
Müller et al.

[11] Patent Number: 6,146,627
[45] Date of Patent: Nov. 14, 2000

[54] METHOD FOR REDUCING T CELL-MEDIATED CYTOTOXICITY IN HIV USING ANTI-IDIOTYPIC ANTIBODY

[75] Inventors: Sybille Müller; Haitao Wang, both of Lexington, Ky.

[73] Assignee: Sidney Kimmel Cancer Center, San Diego, Calif.

[21] Appl. No.: 09/211,156

[22] Filed: Dec. 14, 1998

Related U.S. Application Data

[60] Division of application No. 08/110,348, Aug. 20, 1993, Pat. No. 5,849,583, which is a continuation-in-part of application No. 07/848,327, Mar. 9, 1992, abandoned.

[51] Int. Cl.[7] .......... C07K 16/00

[52] U.S. Cl. .......... 424/131.1; 424/133.1; 424/141.1; 530/387.2

[58] Field of Search .......... 424/131.1, 133.1, 424/141.1; 530/387.2

[56] References Cited

PUBLICATIONS

Askonas et al., "Dominance of a Cell Clone Forming Antibody to DNP," *Nature,* 238:339–341 (1972).

Briles et al., "Clonal Nature of the Immune Response," *J. Exp. Med.,* 152:151–160 (1980).

Oellerich, "Enzyme–Immunoassay: A Review," *J. Clin. Chem. Clin. Biochem.,* 22:895–904 (1984).

Roitt, Groves Medical Publishing Ltd., p. 103 (1985).

Nara et al., "Absence of Cytotoxic Antibody to Human Immunodeficiency Virus–Infected Cells in Humans and its Induction in Animals after Infection or Immunization with Purified Envelope Glycoprotein gp120," *Proc. Natl. Acad. Sci. USA,* 84:3797–3801 (1987).

Riechmann et al., *Nature,* 332:323–327 (1988).

Briault et al., "Isotypy of Serum Monoclonal Immunoglobulins in Human Immunodeficiency Virus–Infected Adults," *Clin. Exper. Immunol.,* 74:182–184 (1988).

Leturcq et al., "Neutralization of HIV–1 by Anti–Idiotypic Antibodies," Fifth Int'l Conf. on AIDS, Montreal, Canada, p. 553 (1989).

Siccardi et al., "Idiotypic Reconstruction of HIV–1 GP41–GP120 Interacting Structures," Fifth Int'l Conf. on AIDS, Montreal, Canada, p. 653 (1989).

Morrow et al., "Anti–Idiotypic Antisera Raised Against Monoclonal Antibody Specific for a p24 gag Region Epitope Detects a Common Interspecies Idiotype Associated with Anti–HIV Responses," *Viral Immunology,* 3:99–109 (Nov., 1990).

Nara et al., "Emergence of Viruses Resistant to Neutralization by V3–Specific Antibodies in Experimental Human Immunodeficiency Virus Type 1 IIIB Infection of Chimpanzees," *J. Virol.* 64:3779–3791 (1990).

Muller et al., Generation and Specificity of Monoclonal Anti–Idiotypic Antibodies Against Human HIV–Specific Antibodies, *J. Immunology,* 147:933–941 (Aug., 1991).

Nara et al., "Neutralization of HIV–1: a Paradox of Humoral Proportions," *FASEB Journal,* 5:2437–2455 (1991).

Montefiori et al., "Homotypic Antibody Responses to Fresh Clinical Isolates of Human Immunodeficiency Virus," *Virology,* 182:635–643 (1991).

Waldmann, "Monoclonal Antibodies in Diagnosis and Therapy," *Science,* 252:1657–1661 (Jun. 21, 1991).

Kang et al., "Evidence for Non–v3–Specific Neutralizing Antibodies that Interfere with gp120/CD4 Binding in Human Immunodeficiency Virus 1–infected Humans," *Proc. Natl. Acad. Sci. USA,* 88:6171–6175 (Jul., 1991).

Matricardi et al., "Spectrotypic Analysis of Anti–gp120 Antibodies in HIV–Infected Patients," VII Int'l Conf. for AIDS, 2:167 (1991).

Halpern et al., "Human Anti–Phosphorylcholine Antibodies Share Idiotopes and are Self–Binding," *J. Clin. Invest.,* 88:476–482 (1991).

*Primary Examiner*—Jeffrey Stucker

*Attorney, Agent, or Firm*—Townsend and Townsend and Crew LLP

[57] ABSTRACT

The present invention provides an anti-idiotypic antibody having specific reactivity with an idiotope common to more than one type of anti-HIV-1 antibody, and having no specific reactivity with non-HIV-1 antibodies. The present invention provides methods of diagnosis, monitoring and treatment of HIV-related diseases through the use of this antibody or related compounds.

3 Claims, 9 Drawing Sheets

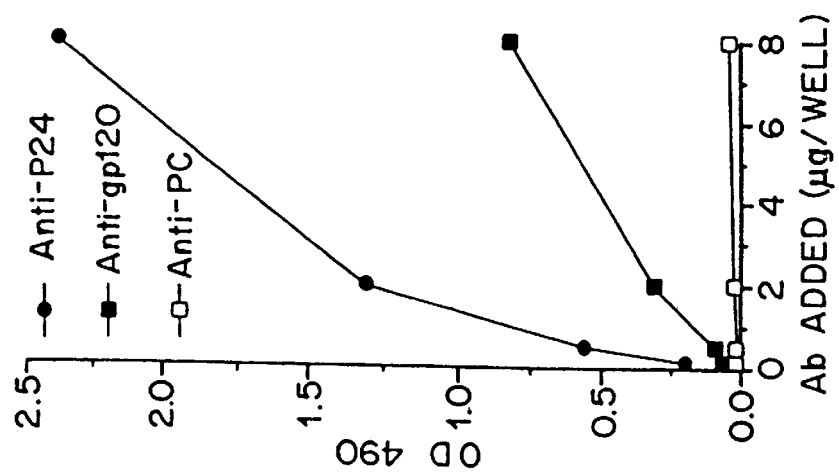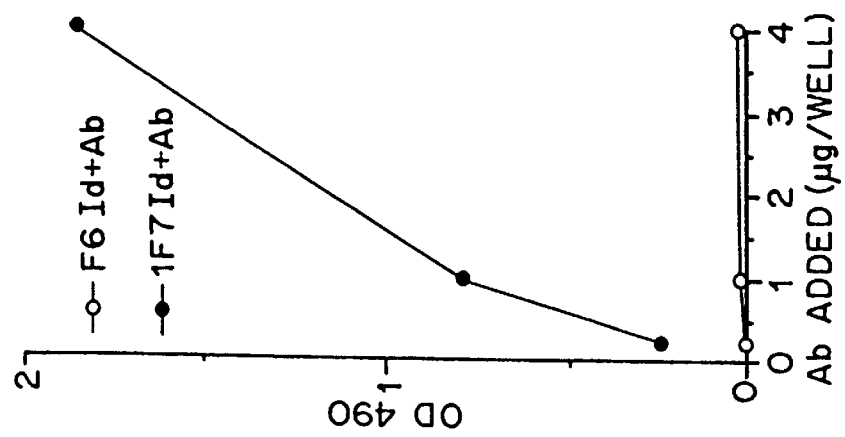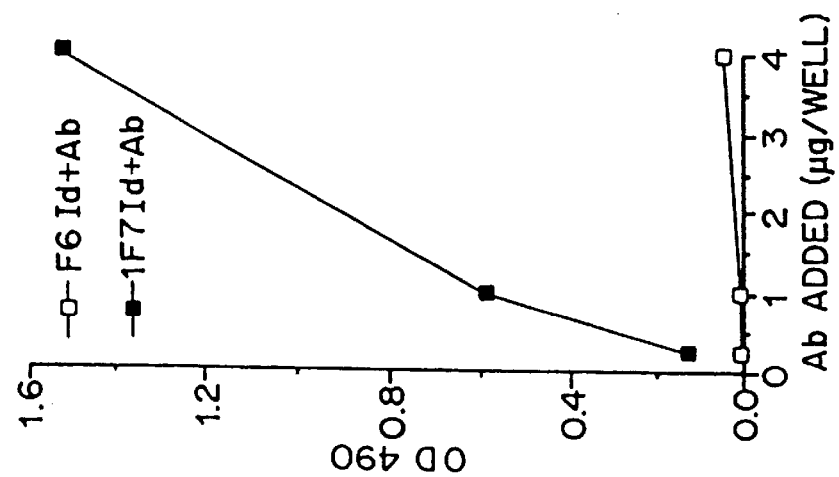

METHOD FOR REDUCING T CELL-MEDIATED CYTOTOXICITY IN HIV USING ANTI-IDIOTYPIC ANTIBODY

RELATED APPLICATIONS

This application is a divisional of Ser. No. 08/110,348, now U.S. Pat. No. 5,849,583, filed Aug. 20, 1993, which is a continuation-in-part of application U.S. Ser. No. 07/848,327, filed Mar. 9, 1992, the contents of which are hereby incorporated by reference abandoned.

ACKNOWLEDGEMENT

This invention was made with the support of government grants RFA-N11-1-NIAID-87-CA-03 and R01CA51434-01 from the National Institute of Health. Therefore, the United States government may have rights in the invention.

BACKGROUND OF THE INVENTION

This invention relates to the diagnosis and treatment of AIDS and more specifically to an anti-idiotypic antibody reactive with more than one type of anti-HIV-1 antibody. The invention further relates to the use of the anti-idiotypic antibody as a diagnostic and therapeutic agent.

Acquired Immune Deficiency Syndrome, or AIDS, has been described as a modern plague. In the decade since its first description in 1981, it has claimed 120,000 victims in the United States alone. Currently almost 200,000 people are known to be infected with the virus. However, the true impact of the disease has yet to be felt. The virus may remain latent in infected individuals for five or more years before symptoms appear. Many Americans may unknowingly be infected and capable of infecting others who might come into contact with their body fluids. Virtually every person who contracts the virus will develop AIDS and die as a consequence. Thus, if unchecked, the personal, social and economic impact of AIDS will be enormous.

The causative agent of AIDS is Human Immunodeficiency Virus Type 1 (HIV-1). The intact HIV-1 virion is roughly spherical and is approximately 110 nm in diameter. The virion has an outer membrane covered with knobs or spikes made up of glycoprotein, gp160/120. In addition, there exists a transmembrane protein termed gp41. Inside the virion are two structural proteins: an outer shell composed of the phosphoprotein p17 and an inner nucleoid or central core made up of the phosphoprotein, p24. The viral RNA is present inside the core along with two copies of the reverse transcriptase enzyme, RT or p65, which is necessary for the synthesis of viral DNA from the RNA template. In an infected person, antibodies are made to each of the aforementioned protein components and exist in characteristic concentrations throughout the course of the disease.

AIDS progresses through three stages after HIV-1 infection. The first is an asymptomatic stage during which the host harbors the virus, tests seropositive for HIV-1 antibodies, but does not exhibit any of the symptoms of HIV-related disease. This stage can last for periods as long as five or more years. The second stage, AIDS-Related Complex (ARC), and the final stage, AIDS, are symptomatic and characterized by tumors and a series of opportunistic infections.

Shortly after HIV-1 infection a vigorous humoral response is initiated. This phase is characterized by elevated levels of circulating antibodies. Specific neutralizing antibodies are directed against the various component proteins of HIV-1 and the initial virus is drastically reduced to levels where it is often difficult to isolate. This point marks the beginning of the disease-free phase of HIV infection with its hallmarks of normal T4 counts and high antibody activity against HIV-1 component proteins. However, despite the presence of cellular and humoral immunity in the infected individual, the virus persists and after several years of latency will become active, often mutating to variant forms, and eventually destroying the immune system leading to full-blown AIDS.

In humans, viral infections are typically cleared by two major classes of immune response, a humoral response mediated by B-lymphocytes which produce antibodies and a cell-mediated immune response directed by T-lymphocytes. Individuals who test positive for HIV-1, however, are unable to clear the infection through these two types of immune response. They may remain positive for several years until they succumb to the opportunistic infections characteristic of AIDS. Thus far no case of viral clearance has been reported. The failure of the immune system to eradicate the AIDS virus after infection remains a mystery of HIV infection. It was first explained as a failure of the cell-mediated response due to the destruction of T helper cells (T4) by HIV-1. However, this explanation is difficult to defend since the T4 count remains normal and only a small fraction of T4 cells appears to be infected during the long latent and asymptomatic phases of the disease.

It is now considered likely that abnormalities in the humoral response of B-cells against HIV-1 is at least in part responsible for the ineffectiveness of the immune system associated with HIV-1-related disease. Instead of the normal polyclonal response seen in other infections, the antibody response in HIV-1 infected individuals appears to result in oligoclonal or monoclonal antibody populations. Briault, et al., *Clinical and Experimental Immunology* 74, 182 (1988).

Traditional methods of diagnosing HIV-1 infection include serological tests to detect the presence of HIV-1 antibodies and polymerase chain reaction for virus detection. However, there are drawbacks to these traditional methods. Although they confirm the absence or presence of HIV-1, they do not indicate the stage of disease progression. Subjects entering the symptomatic stages of disease often fail to recognize the onset of symptoms and delay seeking help. Currently there is no effective treatment for HIV-infection. No effective vaccine is presently available. AZT and other pharmaceutical compounds can temporarily alleviate symptoms in AIDS patients, but have been unable to stimulate the immune system to clear the virus.

Thus, there exists a need for further understanding of the factors which determine the progress of HIV-related disease in order to provide for methods of prevention and treatment of the immune system abnormalities which are characteristic of ARC and AIDS. The present invention satisfies these needs and provides related advantages as well.

SUMMARY OF THE INVENTION

The present invention provides compounds specifically reactive with an idiotope common to more than one type of human anti-HIV-1 antibody. In particular, the invention provides an anti-idiotypic antibody which is specifically reactive with more than one type of human anti-HIV antibody, and not specifically reactive to human non-HIV antibodies. A preferred anti-idiotypic antibody of the present invention is the monoclonal antibody designated 1F7, which is specifically reactive against at least three human anti-HIV-1 antibodies of differing specificities, and non-reactive with human non-HIV antibodies. The idiotope recognized by the anti-idiotypic antibody of the present invention, and in particular the idiotope recognized by the 1F7 antibody, is shown to be involved in the clonal suppression of B cells characteristic of HIV infection. The 1F7 antibody is also shown to influence T cell anti-idiotypic regulation. Therefore, the present invention provides a method of regulating the immune response in HIV-infected individuals through treatment with the anti-idiotypic antibody. This is thought to occur through the selective binding of subsets of B and T lymphocytes by the antibody of the present invention. In addition, the presence of the idiotope recognized by the anti-idiotope antibody of the present invention in the sera of HIV-infected individuals is found to correlate with HIV-related pathologies, in particular HIV-related B cell lymphoma. Therefore, the present invention provides a method of diagnosing and monitoring HIV-related pathologies by the reaction of the HIV-infected sera with the anti-idiotypic antibody of the present invention.

BRIEF DESCRIPTION OF THE DRAWINGS

FIG. 2a shows the binding of 1F7 Id+ and F6 Id+ antibodies to gp120, and FIG. 2b shows the binding of 1F7 Id+ antibodies to p24, while FIG. 2c shows the binding of 1F7 to human antibodies with different specificities.

DETAILED DESCRIPTION OF THE INVENTION ABBREVIATIONS

Figure 1:
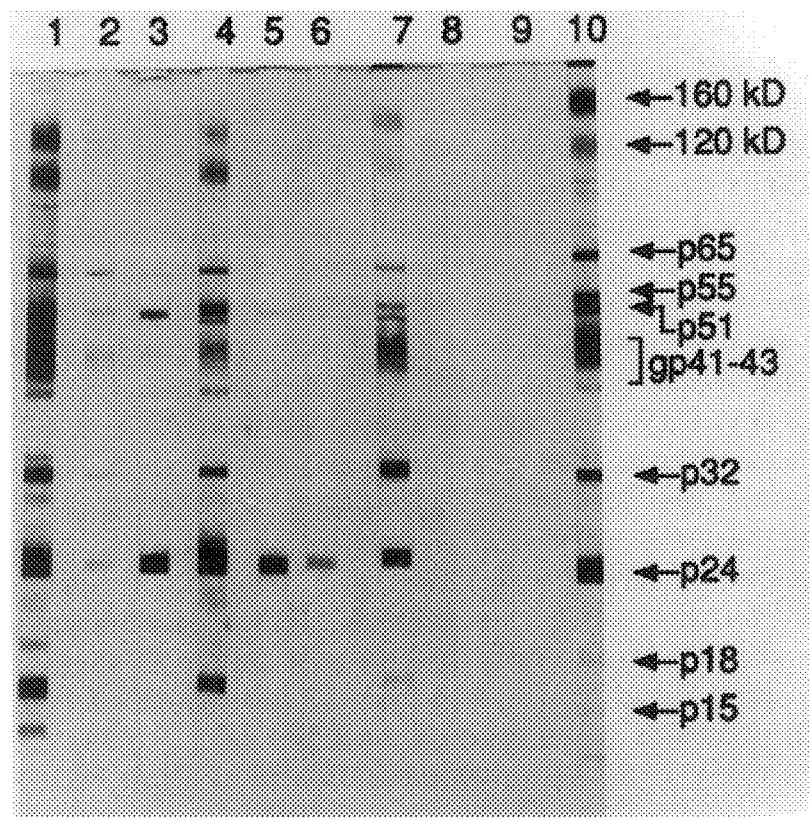
FIG. 1 shows the interaction of the 1F7 antibody with various HIV+ and HIV− sera or purified antibodies.

HIV, human immunodeficiency virus
HIV-1, HIV type 1 virus
HIVIG, human polyclonal anti-HIV immunoglobin
IVIG, pooled human polyclonal immunoglobin
Id, idiotope
Ab, antibody
Id+ Ab, idiotype positive antibodies
V, variable regions of antibody
VH, variable heavy chain
Vk, variable kappa light chain
Vl, variable lambda light chain
gp120, HIV-1 envelope glycoprotein
p24, HIV core protein (gag)
RT, p65, HIV-associated reverse transcriptase
gp160, HIV-1 whole envelope glycoprotein
gp41, transmembrane HIV-associated protein As used herein, the term "HIV-related disease" refers to both the asymptomatic and symptomatic phases, that is the ARC and AIDS phase, which follow HIV-1 infection. The terms "AIDS" and "ARC" refer to Acquired Immune Deficiency Syndrome and AIDS-Related complex, respectively, as described by Adler, *British Medicine,* 294:1145 (1987), which is herein incorporated by reference. AIDS is characterized by tumors and a series of opportunistic infections. As used herein, the term "antibody" refers to any molecule which has specific immunoreactivity activity, whether or not it is coupled with another compound such as a targeting agent, carrier, label, toxin, or drug. Although an antibody usually comprises two light and two heavy chains aggregated in a "Y" configuration with or without covalent linkage between them, the term is also meant to include any reactive fragment or fragments of the usual composition, such as Fab molecules, Fab proteins or single chain polypeptides having binding affinity for an antigen. Fab refers to antigen binding fragments. As used herein, the term "Fab molecules" refers to regions of antibody molecules which include the variable portions of the heavy chain and/or light chain and which exhibit binding activity. "Fab protein" includes aggregates of one heavy and one light chain (commonly known as Fab), as well as tetramers which correspond to the two branch segments of the antibody Y (commonly known as F(ab)$_2$), whether any of the above are covalently or non-covalently aggregated so long as the aggregation is capable of selectively reacting with a particular antigen or antigen family.

As used herein, the term "idiotope" or idiotypic determinant refers to an antigenic determinant or epitope unique to the immunoglobulin product of a single clone of cells. The idiotope is found in the variable region of the antibody. The term "epitope" refers more generally to an antigenic determinant on a molecule which is recognized by antibodies. The term "anti-idiotypic" or "anti-idiotypic antibody" refers to an antibody raised against a first antibody which specifically binds to an idiotope of the first antibody.

As used herein, the term "specificity" is used interchangeably with the terms "specific reactivity" "specifically reactive" and "immunoreactivity". Each term refers to a binding affinity which is greater than background binding. For example, a binding affinity that is measured by an optical density of greater than the standard deviation of the mean optical density of a control as determined by conventional ELISA techniques is considered to represent specific reactivity. Other assays known in the art may also be used to determine specific reactivity. The term "not significantly reactive" is a binding affinity which is not greater than background binding.

As used herein the term "clonotype" refers to the homologous product of a clone of cells, or the phenotype of a clone of cells. Idiotypic determinants expressed by populations of antigen-specific B cells or T cells serve as clonotypic markers for immune cells responding to a given antigenic challenge. Clonotypic specificities may be linked to a single epitope specificity or may be shared by antibodies of different specificities (Zhou, et al. *J. Immun.* 145, 2554 (1990)).

The present invention provides a compound which is specifically reactive with more than one type of human anti-HIV-1 antibody, and not specifically reactive with human non-HIV-1 antibodies. In particular, the present invention provides an anti-idiotypic antibody which is specifically reactive against an idiotope common to more than one type of human anti-HIV antibody, and not specifically reactive with human non-HIV antibodies. A preferred anti-idiotope antibody is the monoclonal antibody 1F7, which specifically reactive with a common clonotype shared by anti-HIV-1 antibodies having different specificities.

The anti-idiotypic antibody of the present invention is useful as a diagnostic and prognostic marker to measure the level of reactive HIV-1 antibodies in samples from HIV-infected patients. Analysis of these levels allows early characterization of HIV-related disease progress, allowing the early diagnosis and treatment of HIV-related pathologies. In addition, the anti-idiotypic antibody is useful therapeutically to facilitate viral clearance. Dominant B-cell clones producing antibodies which express the idiotope against which the antibody is reactive and which are no longer effective against HIV-1 are suppressed, thereby restoring the normal polyclonal immune response which can effectively clear the virus from the infected individual's system.

The anti-idiotypic antibody of the present invention is produced against HIV-infected sera, and then screened for specific reactivity against antibodies reactive against various HIV antigens, and for lack of reactivity against human non-HIV antibodies. The anti-idiotypic antibody is specifically reactive with antibodies reactive against different HIV antigens, such as anti-p24 antibodies, anti-gp120 antibodies and anti-RT antibodies (Id+ antibodies).

The antibody of the present invention may be produced by methods well known in the art. For example, Fabs and methods for making them are described in Harlow and Lane, *Antibodies, A Laboratory Manual,* 626–631 (1988), which is incorporated herein by reference. Examples of reactive single chain polypeptides and a method to generate them are taught by Ladner, U.S. Pat. No. 4,946,778, which is incorporated herein by reference. Antibodies may be produced by monoclonal techniques such as the method of Kohler and Milstein, *Nature* 256, 495 (1975), which may be modified by Gerhard, *Monoclonal Antibodies,* Kennett et al., eds., 370–371 (1980), for example, both of which are incorporated herein by reference. Alternatively, antibodies can be screened from polyclonal selections by well-known assay methods. Antibodies may also be produced by recombinant DNA techniques as taught by Cabilly et al., U.S. Pat. No. 4,816,567, for example, which is herein incorporated by reference, or selected from immunoglobulin combinatorial libraries as taught by Huse, et al., *Science* 246, 1275 (1989), which is also incorporated by reference. CDR grafting as taught by Cabilly et al., supra, can also be used to produce fragments reactive with the idiotope.

In addition, the invention provides an isolated idiotope found to be common to several types of HIV-1 antibodies (Id+ antibodies), particularly those produced by dominant restricted B-cell clones, and specifically reactive with the anti-idiotypic antibody of the present invention. This idiotope, when recognized and isolated from an Id+ antibody, or otherwise synthetically or recombinantly produced, is useful in the production of monoclonal and polyclonal antibodies for diagnostic, prognostic and therapeutic applications using techniques well known in the art. For example, the isolated idiotope may be used to immunize animals to generate hybridomas expressing monoclonal antibodies specific for the idiotope. In other cases, the idiotope may be used to stimulate an immune response in a rabbit, goat, non-human primate or other animal from whose serum polyclonal antibodies may be obtained by methods well known in the art. In addition, the idiotope may be used for the purification or characterization of anti-idiotypic antibodies of interest, for example, monoclonal antibodies or antibodies present in human tissue or body fluids.

In addition to antibodies, the methods of the present invention can employ non-antibody compounds which have a binding affinity for the idiotope recognized by the antibody of the present invention, and which do not bind to non-HIV antibodies. Such compounds can be constructed according to methods known in the art and include peptide or non-peptide drugs, for example, which have a specific binding affinity for the recognized idiotope.

The present invention provides a method of restoring oligoclonality in the antibody response to HIV infection through the administration of the anti-idiotypic antibody or other reactive compound of the present invention to an HIV+ individual. Anti-idiotypic regulation can enforce oligoclonality either by suppressing the dominant B cell response to HIV or reinforcing the growth of other clones. This approach to treatment is based on the particular characteristics of HIV infection.

During the time HIV-1 inhabits the host, its major neutralizing epitopes, particularly gp120, undergo rapid mutations giving rise to neutralization-escape variants. Nara, et al., *Journal of Virology* 64, 3779 (1990); Nara, et al., *FASEB Journal* 5, 2437 (1991). It is thought that the antibodies which were produced in response to the initial HIV-1 infection are not effective against the new escape variants and that the host immune system fails to produce new antibodies to the variants. Montefiori et al., *Virology* 182, 635 (1991); Nara et al. *J of Virology* 64, 3779 (1990); Nara et al., *PNAS USA* 84, 797 (1987). The failure of the immune system to recognize these newly-emerging virus isolates is thought to be due to the establishment of a dominant clonal population of B-cells committed, or restricted, to producing antibodies to the original HIV-1 variant. The dominant clones prevent the recruitment and expansion of other B-cell populations which could be capable of an effective response to new HIV-1 variants and other opportunistic viruses. In other settings, dominantly established B-cells have been found to exert a suppressive effect on minor B-cells which are directed against the same or cross-reactive epitopes. Askonas and Williamson, *Nature* 238, 339 (1972); Briles and Davie *J Exp Med* 152, 151 (1980).

It appears that as HIV-1 generates neutralization escape variants, the mutated epitopes retain sufficient cross-reactivity to continue to trigger the early, clonally expanded B-cell clones. Evidence for this cross-reactivity with envelope epitopes has been observed in divergent isolates. Kang et al., *PNAS USA* 88, 6171 (1991). Thus, B-cells with potentially higher affinity for mutated epitopes may be limited in their ability to respond and proliferate to reach an effective clone size. Instead, cross-stimulation by mutated HIV-1 epitopes continues to trigger and expand the original and now ineffective clones. Recent reports on constant IEF profiles over time in infected individuals document the persistence of anti-gp120 specific B-cell clones. Matricardi, et al., *Seventh International Conference for AIDS* 2, 167 (1991). By this mechanism a situation can develop in which the infected individual produces human neutralizing antibodies that are effective against laboratory strains and isolates from different seropositive individuals, but less effective against the autologous HIV-1 variants. Montefiori et al. supra, (1991); Nara, et al., supra (1990).

The approach to treatment of HIV infection provided by the present invention is based on the surprising discovery that idiotope common to more than one type of HIV-1 antibody is produced by restricted B-cell clones. Clonal restriction of B-cells producing these antibodies has been demonstrated by kappa/lambda light chain analysis, isoelectric focusing, and immunoblot analysis of variable region diversity of B-cell colonies responding to HIV-1 infection, as demonstrated in Example III below.

A preferred anti-idiotypic antibody is the monoclonal 1F7 antibody. The production and screening of 1F7 is described in Example 1 below. A hybridoma cell line capable of expressing the 1F7 antibody has been deposited with the American Type Culture Collection in Rockville, Md., and has been assigned ATCC No. HB 11286.

1F7 is found to be specifically reactive with at least three anti-HIV antibodies having separate specificities. It is shown in Example II below that the 1F7 Id is a clonotype marker for anti-HIV antibodies. A clonotypic analysis of HIV+ and HIV− sera demonstrates that it is common for the 1F7 Id clonotype to be shared by different anti-HIV-1 antibodies produced by the same HIV+ individual (see Western blot, FIG. 1, and TABLE 2). Because a shared clonotypic marker on B cells responding to HIV infection would be expected to be the target of regulation and maintenance of the immune response to the HIV virus, the 1F7 Id is considered to be involved in anti-idiotypic regulation of the immune system in HIV-infected persons.

Evidence is provided that anti-HIV+ antibodies and 1F7 Id+ antibodies in particular are of restricted clonal origin. This is demonstrated by the data shown in Example III A, B, and C below.

Therefore, the present invention provides a method of overcoming the dominance of the ineffective clones by blocking the idiotope recognized by the anti-idiotypic antibody of the present invention. Treatment of a patient with the compound of the invention will result in the specific binding of the antibody or related compound to the idiotope on cells in the dominant clones. This results in the inhibition of their proliferation and curtailment of the production of antibodies to the original HIV-1 variant. As a result of the dominant cells being blocked, other B-cells are able to respond to the new HIV-1 variants. A normal polyclonal immune response is restored and antibodies to the new HIV-1 variants are effective in clearing the virus from the host system.

It is further shown that T cells in HIV+ infected persons may be subject to anti-idiotypic regulation via the idiotope recognized by 1F7. T cells from HIV+ sera sample were analyzed for evidence of anti-idiotypic regulation by the 1F7 anti-idiotypic antibody as described in Example V below. Peripheral Mononuclear Blood Cells (PMBC) were taken from sera from HIV+ individuals and HIV− normal control individuals and grown in culture according to the methods described in Example V below. These cells were exposed to the 1F7 antibody and an isotype control antibody. It was found that the 1F7 antibody induced apoptosis in 16 of the 20 HIV+ samples, and none of the HIV+ control samples. Flow cytometric analysis and lymphocyte subset depletion experiments described in Example V below demonstrated that cells undergoing apoptosis were the T cells subset CD8+ cells. These findings indicate that 1F7 binds a subset of T-lymphocytes selectively expanded in HIV infection through receptor molecules linked to cell-mediated apoptosis. In addition, the experiments described in Example VI below demonstrate that 1F7 reduces T-cell mediated cytotoxicity in HIV+ sera. Because CD8+ cytotoxic T-lymphocytes (CTL) are known to circulate in HIV-1 infected individuals (Walker et al., Nature 328, 345 (1987)), a reduction in CTL activity in response to 1F7 is another indication that 1F7 is capable of influencing the composition of T cells in HIV-infected individuals. Therefore, by selectively binding to subsets of B and T lymphocytes expanded during HIV infection, the antibody of the present invention is expected to favorably alter the immune response in HIV infection.

In another aspect of the present invention, the presence of the idiotope recognized by the antibody of the present invention in a sample of human sera is found to correlate with the occurrence of HIV-related pathologies in the individual. As described in Example IV, the recognition of the 1F7 idiotope on IgG and IgM correlates with the HIV+ condition, and in particular correlates with the occurrence of HIV-1 related lymphoma. Studies show that 93% of HIV-1 infected patients with lymphoma test positive for 1F7 expression. Therefore, the detection of the 1F7 idiotope by reaction with the 1F7 antibody is a method of predicting, detecting, or monitoring the occurrence of HIV-1 related lymphoma in HIV+ patients. The detection and diagnosis of the lymphoma at an early stage is particularly useful because it allows for a more aggressive and suitable treatment of this particular malignancy.

The invention further relates to use of the antibody or non-antibody compound of the present invention to detect certain types of HIV-1 antibodies in a sample. This can be useful for identifying HIV-1 antibodies in cells or other samples being prepared for laboratory use, or in samples from patients suspected of having HIV-related disease. One embodiment involves contacting the sample suspected of containing HIV-1 antibodies with the antibody or compound of the present invention and determining whether binding occurs. For example, a sample from a patient might be serum, semen, urine, tissue, cells or any other sample generally known or suspected to contain antibodies. A sample might also be spent culture from cell lines being tested for HIV-1 antibody production. The antibody is most easily put in contact with the sample by mixing them together in a test tube or in the depression well of a slide. Subsequent determination of binding may be performed by any means known in the art, for example, radioimmune assay, staining of labelled compound, or immunoprecipitation. Binding affinity above background indicates the presence of HIV-1 antibodies and is diagnostic of HIV-related disease.

In addition, the invention relates to the use of the antibody or non-antibody compounds of the present invention to obtain a quantitative determination of HIV-1 antibody level in order to prognose a patient's HIV-related disease progression so that effective therapy can be initiated. As used herein, the term "prognose" of "prognosing" refers to monitoring the progression, determining the prognosis or forecasting the appearance of symptoms of HIV-related disease. Previous methods of plotting T4 cells and antibody levels have proven unsatisfactory as sole prognostic tools. The levels of HIV-1 antibody obtained by practicing the present invention are the result of the reliable, progressive development of clonal dominance of B-cell colonies. The antibodies produced by these colonies exhibit the novel idiotype and bind to the antibody or compound of the invention. Quantitative results regarding binding may be obtained as described above. The amount of binding determined by the procedure is compared to a standard for the various stages of HIV-related disease. In this way, it is possible to determine the stage of the patient's disease and prognose the development of further symptoms. The standard could be prepared, for example, by the methods described above using fluid samples from patients with symptoms known to characterize specific stages of HIV-related disease and determining the amount of HIV-1 antibody specifically reactive with the antibody or Id-reactive compound of the invention. Resulting levels of antibody are charted against time correlating to stage of progression. The resultant chart serves as the standard on which results from patients of unknown diagnosis and prognosis are plotted. The stage of progression and prognosis of the patient's disease is determined by comparison of his level of HIV-1 antibodies which react to the antibody or non-antibody compound compared to the standard. The 1F7 antibody of the present invention, for example, has been shown, for example, to be particularly precise in monitoring HIV-related lymphoma.

The invention further relates generally to methods for the prevention, immunization and treatment of HIV-related disease by administering an effective amount of the compound to a patient diagnosed with HIV-related disease. An effective amount of antibody to treat HIV-related disease is the amount necessary to produce the effect of destroying clonal dominance of restricted B-cells or restricted or infected T cells, thus restoring a polyclonal immune response in the patient. The compound may be provided as a pharmaceutical composition containing an effective amount of the compound together with a physiologically acceptable carrier. This composition may be administered by any means known in the art, for example, intravenous, intramuscular, subcutaneous, intradermal, intraperitoneal, or by infusion. The compound may also be bound to a suitable therapeutic agent such as a toxin, hormone, drug or other compound to facilitate the destruction of dominant B-cells. Drugs include, in general, alkylating agents, antiproliferative agents, tubulin-binding agents, cytotoxins, and the like. Toxins suitable as therapeutic agents include podophyophyllotoxins, ricin, the trichothecenes, the colchicenes and pseudomonas endotoxin.

The following examples are intended to illustrate but not limit the invention. While they are typical of those that might be used, other procedures known to those skilled in the art may be alternatively employed.

EXAMPLE I

Isolation and Characterization of Anti-idiotypic Antibody

1. Materials

Human polyclonal anti-HIV immunoglobulin (HIVIG), lot VH 102 was obtained from NIAID AIDS Research Reference Reagent Program (ERC Bioservices Corporation, Rockville, Md). Human pooled IgG (IVIG) was purchased from Cutter Biological, Elkhart, Ind. Normal human HIV-sera was obtained from the San Diego Regional Blood Bank. HIV positive (HIV+) sera from healthy, seropositive individuals were obtained from North American Biological Inc. (NABI), Miami, Fla.

Recombinant p24 (HTLV-IIIB) and the p24/gp41 fusion protein were obtained from Dr. Torsten Helting, Pharmacia Genetic Engineering, La Jolla, Calif. Recombinant gp120 (HTLV IIIB), or gp120 (MN) V3 loop peptides, and recombinant HIV-1 reverse transcriptase (RT, p65) were purchased from American Biotechnologies, Inc., Cambridge, Mass. Recombinant gp120 (SF2) was obtained from Chiron Corporation, Emeryville, Calif. The antigen designations IIIB, MN, SF2, etc. refers to laboratory strains of HIV-1.

Human monoclonal anti-HIV-1 antibodies were previously described in the publications of Gorny et al., *PNAS USA* 88, 3228 (1991), and Gorny et al., *PNAS USA* 86, 1624 (1989), which are both herein incorporated by reference. These include human monoclonal anti-p2$^4$ antibodies, 71-31, 91-5, and 241-D (all IgG1, lambda), anti-gp120 antibodies, 257-D, 268-D, and 453-D (all IgG1, lambda) and anti-gp41 antibody 98-6 (IgG2, kappa).

2. Methods

1. Production of mouse monoclonal antibody against human polyclonal HIVIG

Monoclonal antibodies were produced according to the method of Muller et al., *J Immun* 147, 933 (1991), which is herein incorporated by reference. BALB/c mice (MTS Laboratories, San Diego, Calif.) received three subcutaneous injections of 50 μg of human HIVIG in Freund's complete and incomplete adjuvant (Sigma Chemical Co. St. Louis, Mo.) on days 1, 10 and 20. On day 45 the mice were boosted with 50 μg HIVIG intravenously. Mouse splenic cells were then fused with Sp2/0 cells according to standard protocols. Culture supernatants were screened as described below.

Microtiter plates were coated with 100 μl/well of 2 μg/ml of either gp120 or p24 in bicarbonate buffer (pH 9.6) at 4° C. overnight, and blocked with 2% BSA for two hours following by adding 100 μl/well of 100 μg/ml of HIVIG and incubated for two hours. After washing three times with 0.01 M PBS containing 0.1% Tween-20 (PBS-T), 100 μl of hybridoma culture supernatants were added and incubated for two hours. After washing another three times, 100 μl of $10^5$ cpm $^{125}$I-labeled goat anti-mouse Ig were added to each well and incubated at 37° C. for 1.5 hours. The plates were washed three times and cut for counting to determine cpm bound to each well in the gamma counter (Nuclear-Medical Laboratories, Inc.).

Alternatively, replicas of the microtiter plates were coated with 100 μl/well of 2 μg/ml of IVIG (Cutter Biological, Elkhart, Ind.) at 4° C. overnight, then blocked with 2% BSA. IVIG, which refers to human pooled IgG from human sera not containing HIV antibodies, which is generally derived from a large donor pool of greater than 10,000 donors. The subsequent procedure of adding culture supernatants and $^{125}$I-labeled goat anti-mouse Ig was the same as described above. Hybridoma antibodies which bound to antibodies captured by HIV antigens, not to IVIG, were selected.

Positive clones were subcloned four times and expanded in tissue culture flasks or amplified by ascites in BALB/c mice. Monoclonal antibodies of IgM isotype derived from supernatants and ascites were purified on goat anti-mouse IgM Sepharose 4B column (Pharmacia LKB, Biotechnology AB, Uppsala, Sweden).

3C1, another IgM kappa clone from the same fusion as produced 1F7, is used as a negative control in several experiments.

2. Western blot analysis

Western blot analysis was performed using commercial HIV-1 Immunoblot Kits according to manufacturer's instruction (Bio-Rad, Hercules, Calif.). For detecting human anti-HIV antibodies, human sera or 1F7-purified human antibodies were incubated with nitrocellulose strips containing HIV-1 antigens for 30 minutes. After washing, the antibodies that bound to HIV antigens were detected using alkaline phosphatase-conjugated goat anti-human IgG. For detection of 1F7 positive anti-HIV antibodies captured by HIV antigens, the nitrocellulose strips were first incubated with human sera for 30 minutes. After washing two times, 3 ml of 1F7 supernatants were added to each strip, and incubated for 2 hours. After repeatedly washing, each strip was incubated for one hour with 3 ml of peroxidase conjugated-goat anti-mouse IgM (1:200 dilution, Fisher Biotech, Pittsburgh, Pa.). The development of the strips was performed using 3 ml of 600 µg/ml of diaminobenzidine (DAB) (Sigma Chemical Co., St. Louis).

3. Affinity Purification of human serum antibodies

Immunoaffinity purification of human serum antibodies was performed by coupling recombinant p24 protein, recombinant p24/gp41 fusion protein and mouse anti-idiotypic antibody, 1F7, respectively to CNBr-activated Sepharose 4B (Pharmacia LKB, Biotechnology AB, Uppsala, Sweden) according to the manufacturer. The purification of anti-phosphorycholine (PC) and F6 Id+ antibodies (F6 idiotype positive antibodies) was carried out as described in Halpern, et al. *J. Clin. Invest.* 88, 476 (1991), which is herein incorporated by reference. F6 is an unrelated anti-idiotypic antibody which reacts with natural human anti-PC antibodies, and is used as a control in experiments involving 1F7. In order to obtain anti-gp41 antibodies on a p24/gp41 affinity column, HIV+ serum was first absorbed repeatedly on p24 affinity column to remove anti-p24 antibodies totally. The flow-through was then passed over p24/gp41 immunoabsorbent.

Sera from HIV+ individuals was diluted with 0.01 M PBS, pH 7.0, and applied to immunoabsorbents. After extensive washing with PBS, bound antibodies were eluted with 0.1 M glycine buffer (pH 2.5), dialyzed against PBS and concentrated.

4. ELISA for detection of human antibodies to gp120 and p24

The recombinant gp120, RT, or p24 were coated in microtiter plates at 100 µl/well of 2 µg/ml overnight at 4° C., then blocked with 2% BSA. Human sera or purified human antibodies diluted in 0.01 M PBS containing 0.1% Tween 20 (PBS-T) and incubated for 2 hours. Wells were then incubated with peroxidase conjugated-goat anti-human IgG (1:5000, TAGO, Inc., Burlingame, Calif.) for one hour. All incubations were followed by washing five time s with PBS-T. Bound antibodies were visualized using O-phenylenediamine (OPD)(Sigma Chemical, St. Louis), and the reaction was stopped with 3N $H_2SO_4$. Optical density (OD) was read at an absorbance of 490 nm (Molecular Devices Corporation, Menlo Park, Calif.).

5. ELISA for determination of 1F7 Id expression on anti-p24, anti-p120 antibodies, and anti-RT antibodies This procedure was similar to the HIV antigen-capture RIA for detection of anti-HIV antibodies described above. Microtiter plates were coated with 200 µg/well of gp120 (IIIB or SF2), RT, or p24 at 4° C. overnight, then blocked with 2% BSA. Human sera (1:100 dilution) or affinity-purified human antibodies were added to each well and incubated for 2 hours. After washing, 100 µg/well 1F7 supernatants or 3C1 (a control mouse monoclonal IgM) supernatants were added and incubated for 2 hours, followed by additional washing. 1F7 or 3C1 bound to antibodies captured by gp120, RT or p24 were detected with peroxidase conjugated-goat anti-mouse IgM.

6. ELISA for Competitive Inhibition of Binding of 1F7 Id+ antibodies to gp120 and p24 by 1F7.

The procedure of coating, washing, and developing of microtiter plates was performed as described above, except that the 1F7 Id+ antibodies, which were purified by 1F7 immunoabsorbent from HIV+ serum were pre-incubated with inhibitors at 4° C. overnight before being added to the plates coated with gp120 or p24. The percent of inhibition was calculated as follows:

$$\% \text{ inhibition} = 100 \times \left(1 - \frac{\text{OD with inhibitor}}{\text{OD without inhibitor}}\right)$$

7. ELISA for identification of human anti-HIV antibodies binding with 1F7

Microtiter plates were coated with 500 ng/well of 1F7 at 4° C. overnight and blocked with 2% BSA for two hours. 100 µl of diluted human sera or human antibodies purified by affinity chromatography, were added to each well and incubated for two hours at room temperature. After washing five times, the plates were incubated with peroxidase conjugated-goat anti-human IgG for 1.5 hours.

Alternatively, 100 µl/well of 1 µg/ml of Biotin-labeled 1F7 were added and incubated for one hour. The plates were washed another five times and then 100 µl/well of avidin-labeled peroxidase (1:2000, Sigma Chemical, St. Louis) was added and incubated for 45 minutes. Subsequent procedure of this assay is as described above. Biotinylation of 1F7 was performed as described by Harlow and Lane, eds. *Antibodies, A Laboratory Manual* (1988), which is herein incorporated by reference.

Procedure

Mouse monoclonal anti-idiotypic antibodies were prepared as described above against HIVIG. Antibodies against HIVIG were detected using p24 and gp120 capture ELISA assays. One hybridoma, 1F7 (IgM, kappa) which bound to antibodies captured by these HIV-1 antigens, but not to IVIG was subcloned and grown as ascites fluid as described above.

Testing using HIVIG and IVIG antibody capture ELISA using p24 and p120 antigens as shown in TABLE 1 showed that sera from HIVIG immunized mice bound to HIVIG captured by p24 or gp120 and also to IVIG, while pre-immune sera did not bind to HIVIG or IVIG. Supernatant from 1F7, however, only bound to HIVIG captured by HIV-1 antigens. The binding of 3C1 was used as a negative control.

TABLE 1

|  | p24-HIVIG | gp12-HIVIG | IVIG |
|---|---|---|---|
| pre-immunized sera | 300 | 400 | 450 |
| post-immunized sera | 24000 | 21600 | 22300 |
| 1F7 | 10400 | 6300 | 550 |
| 3C1 | 670 | 690 | 600 |

Western blot analysis was then performed. Three different reactivity profiles were distinguished using sera from different HIV+ individuals, as shown in FIG. 1. #14 HIV+ serum produced several bands in the p18, p24, gp41 and p55, p65 and gp160 positions when reacted with 1F7 supernatant. #14 HIV+ serum antibodies were purified on 1F7 immunoabsorbent as described above and also analyzed by Western blot. Antibodies purified by 1F7 immunoabsorbent showed binding patterns very similar with that produced by this serum with 1F7. Serum and 1F7 purified from #3 HIV+ serum showed bands only in the p24 and p55 regions. #16 HIV+ serum showed no bands. All three HIV+ sera produced bands with multiple HIV-1 antigens when nitrocellulose strips were developed with alkaline phosphatase-conjugated goat anti-human IgG. FIG. 1 is as follows: lane 1: HIV+ patient #14 serum, developed with goat anti-human IgG; lane 2: HIV+ patient #14 serum, incubated with 1F7 and developed with goat anti-mouse IgM; lane 3; 5 μg of 1F7 affinity purified antibody from patient #14, developed with goat anti-human IgG. lane 4: HIV+ patient #3 serum, developed with goat anti-human IgG; lane 5: HIV+ patient #3 serum, incubated with 1F7 and developed with goat anti-mouse IgM; lane 6: 5 μg of 1F7 affinity purified antibody from patient #3, developed by goat anti-human IgG. lane 7: HIV+ patient #16 serum, developed with goat anti-human IgG; lane 8: HIV+ patient #16 serum, incubated with 1F7 and developed with goat anti-mouse IgM; lane 9: HIV negative control serum, developed with goat anti-human IgG; lane 10: HIV positive control serum, developed with goat anti-human IgG. All human sera were diluted 1:100.

Since the Western blot analysis shown in FIG. 1 showed binding of 1F7 to anti-core and anti-envelope antibodies from #14 HIV+ serum, these antibodies were purified from #14 HIV+ serum by 1F7 immunoabsorbent as described above. The absorbed material on the column was eluted with acid to yield 1F7 Id+ material. Eluted material was concentrated and tested for binding to p24 and gp120 in an ELISA as described above. In FIG. 2a the binding of 1F7 Id+ antibodies to insolubilized gp120 is shown. For a control, #14 HIV+ serum was absorbed on an unrelated anti-ID, F6. Binding to insolubilized gp120 is shown in FIG. 2b. In FIG. 2c, eluted Ig from the p24 affinity column binds strongly to insolubilized 1F7. The flow through from the p24 column was absorbed on and eluted from a chimeric antigen p24/gp41 affinity column. Only residual binding of anti-gp41 antibodies to 1F7-coated plates was obtained indicating that the majority of 1F7 Id+ antibodies are p24 specific in this serum. As a control, anti-PC antibodies purified from HIV+ serum to 1F7 were employed, as seen in FIG. 2c. To obtain the results shown in FIG. 2, microtiter plates were coated with 200 μg/well of gp120 or p24 and then incubated with human antibodies purified by 1F7 or F6 immunoabsorbent. FIG. 2c shows the binding of 1F7 to human antibodies with different specificities. 1F7-coated plates were incubated with human antibodies purified by HIV antigen or PC affinity column. The antibodies bound to 1F7 were detected with biotinylated 1F7 as described above. All human antibodies were purified from #14 HIV+ serum.

Figure 3A:
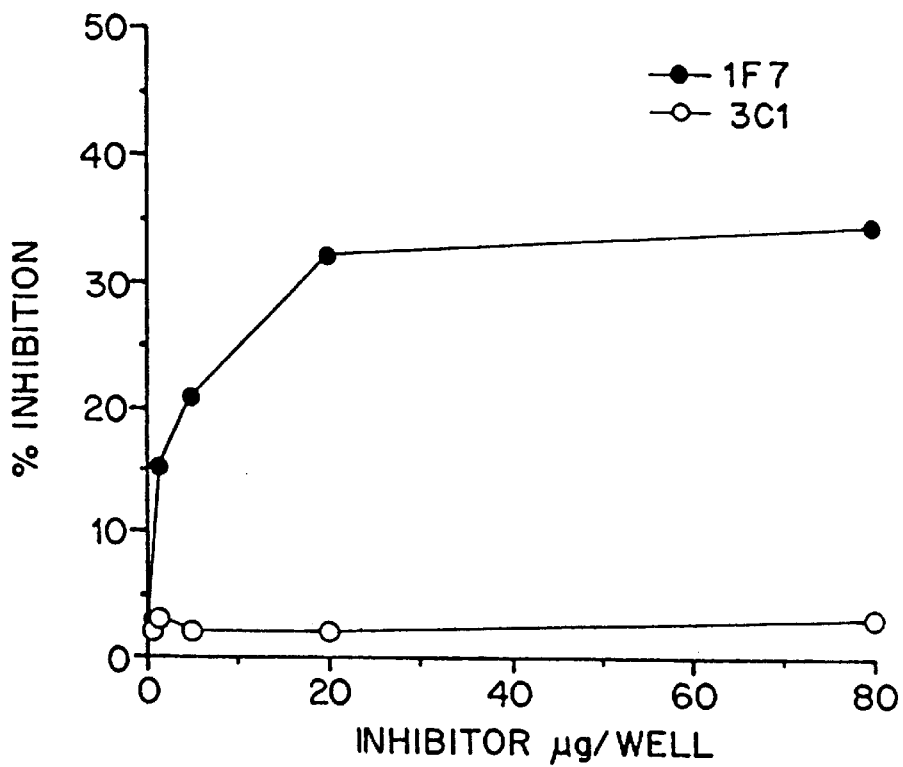
FIG. 3a shows the inhibition of binding of 1F7 Id+ antibodies to gp120 by 1F7.
Figure 3B:
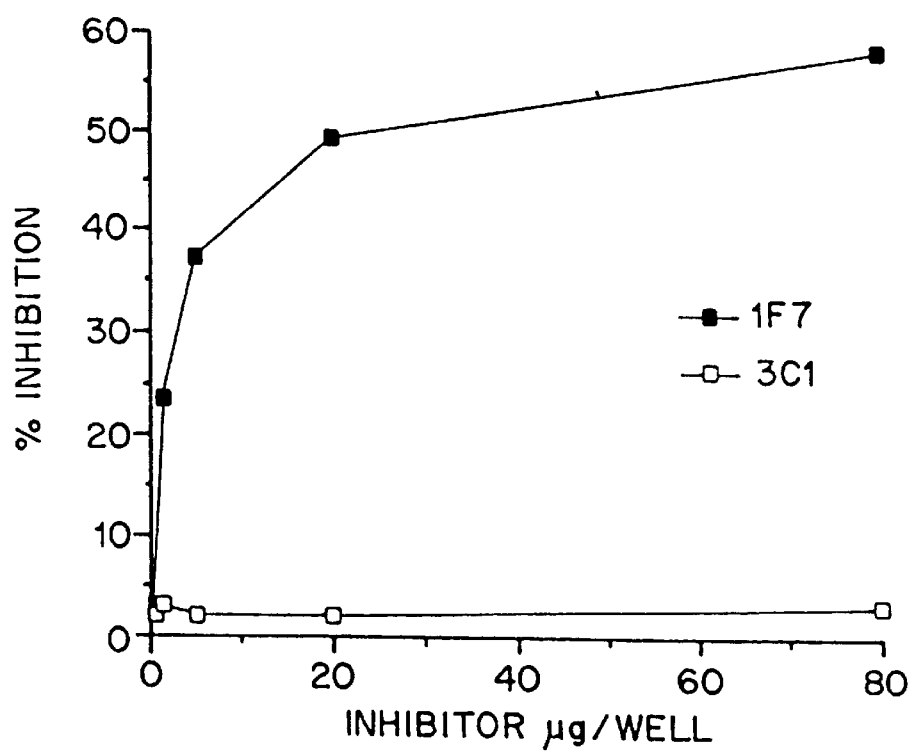
FIG. 3b shows the inhibition of 1F7 Id+ antibodies to p24 by 1F7.

FIGS. 3a and 3b show inhibition of binding of purified 1F7 Id+ antibodies to gp120 and p24 respectively by 1F7. Plates were coated with either gp120 or p24. 1F7 Id+ antibodies were added together with dilutions of 1F7 or a control mouse IgM monoclonal antibody, 3C1, as described above.

EXAMPLE II

Clonotypic Analysis of HIV+ and HIV− Human Serum

According to the Western blot show in FIG. 1 described above, three 1F7 reactivity patterns with HIV+ sera were observed. In one group, represented by #14 HIV+ serum, 1F7 reacted to antibodies to more than one HIV antigen. In the second group, represented by #3 HIV+ serum, 1F7 showed reactivity only with anti-core (p24) antibodies. Serum from the third group showed no 1F7-positive anti-HIV antibodies.

Further testing was performed in order to analyze the representation of these three groups in HIV+ sera. The detection of anti-gp120 and anti-p24 antibodies, and in addition, the detection of 1F7 Id+ on antibodies against gp120 and p24 in HIV+ sera was determined as follows. First, anti-HIV antibodies were detected as described above, by coating microtiter plates with 200 μg/well of gp120 or p24. A 1:40 dilution of HIV+ individual serum was added and incubated. The antibodies which bound to gp120 and p24 were determined by peroxidase conjugated-goat anti-human IgG. For detection of binding of 1F7 to anti-HIV antibodies, the plates coated with gp120 and p24 were first incubated with 1:40 diluted HIV+ sera, then 1F7 supernatants were added and incubated. The binding of 1F7 to anti-HIV antibodies captured by gp120 or p24 was detected with peroxidase conjugated-goat anti-mouse IgM. Bound antibodies were visualized using O-phenylenediamine (Sigma, St. Louis, Mo.), as described above, and the optical density read at 490 nm.

Figure 4A:
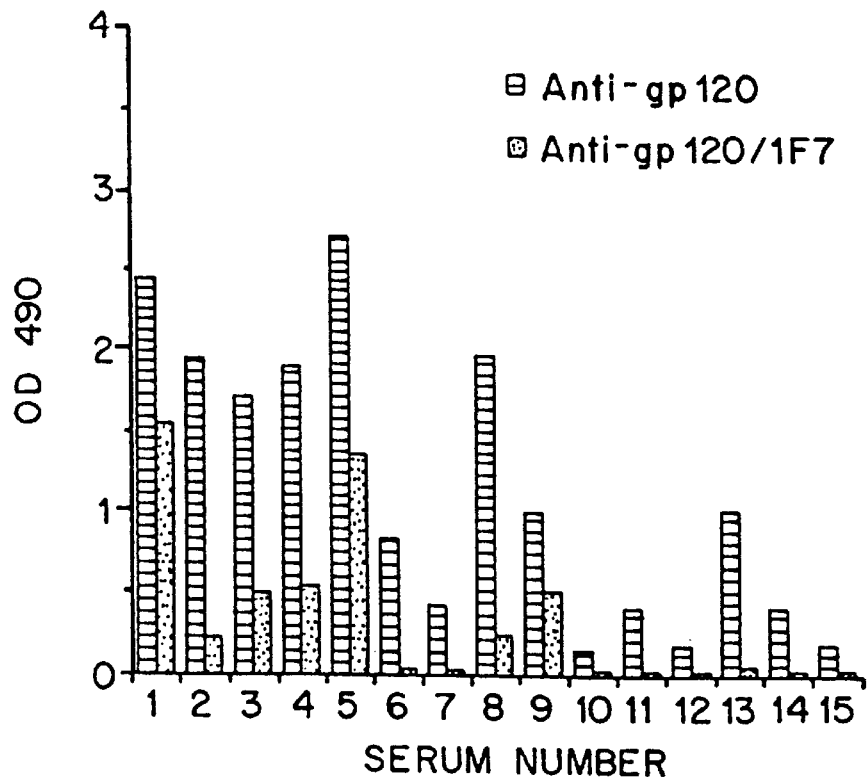
FIG. 4a shows the detection of 1F7 Id expressed on antibodies against gp120 in HIV+ sera.
Figure 4B:
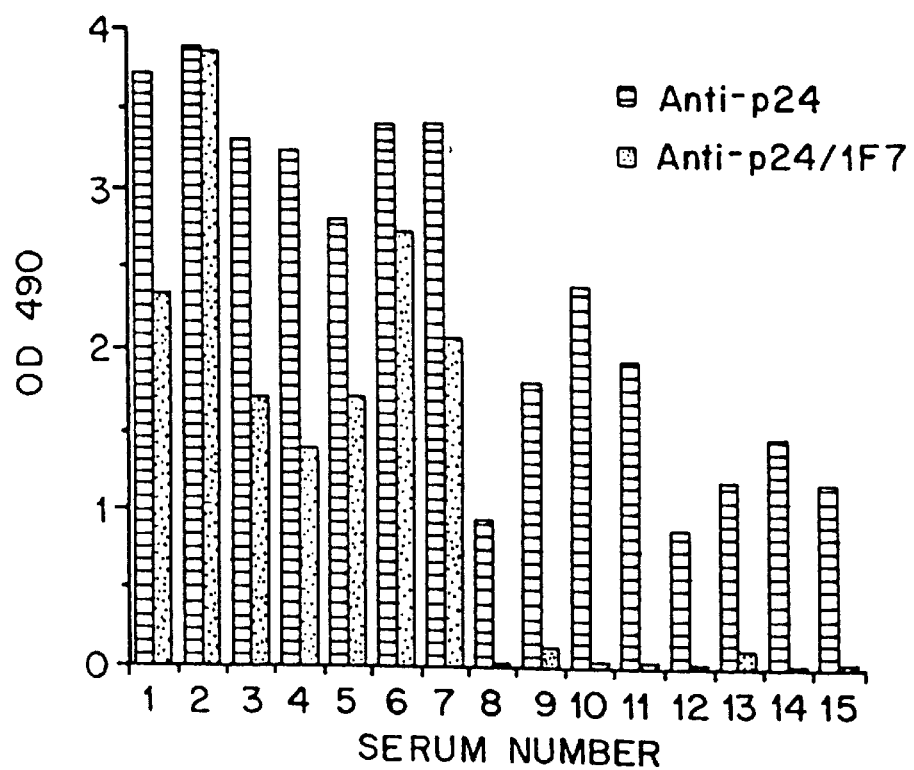
FIG. 4b shows the detection of 1F7 Id expressed on antibodies against p24 in HIV+ sera.

The results are presented in FIG. 4. FIG. 4a shows the anti-gp120 antibodies and anti-gp120/1F7 antibodies detected for each of the 15 HIV+ samples. FIG. 4b shows the anti-p24 and anti-p24/1 F7 antibodies detected for the same 15 HIV+ sera samples. In the 15 HIV+ sera samples, 5 show anti-p24 and anti-gp 120 antibodies. In two sera, only anti-p24 antibodies are 1F7 reactive, and in another 2 sera anti-gp120 antibodies are 1F7 positive. The remaining six HIV+ sera are negative for 1F7. These data indicate that it is not uncommon for the 1F7 Id clonotype to be shared by different antigen-specific antibodies.

To further corroborate the prevalence of idiotope sharing anti-HIV-1 antibodies, HIV-1 antigen capture ELISA, as described in Example 1, was used to detect expression of 1F7 Id on different anti-HIV-1 antigens in sera from 40 HIV-1+ individuals. This procedure is described in Wang et al., *Eur. J. Immunol.* 22 1749 (1992), which is herein incorporated by reference.

Microtiter plates were coated with p24, gp120 (IIIB or SF2), RT and tetanus toxoid (used as a control, obtained from Pharmacia), all 200 μg/well respectively, then blocked with 2% BSA. HIV-1+ sera diluted 1:100 with PBS were added and incubated for 2 hours. After washing, the plates were incubated with 1:5000 diluted peroxidase-conjugated goat anti-human IgG for 1.5 hour. Bound antibodies were visualized using OPD (O-phenylenediamine) at 490 nm. The ELISA for 1F7 Id was similar. After incubation of HIV-1+ sera (1:100) with plates coated with HIV-1 antigens and tetanus toxoid, 100 μg/well of 1F7 were added, and incubated for another 2 hours. After washing, the plates were incubated with 1:2000 peroxidase-conjugated goat anti-mouse IgM for 1.5 hour. The subsequent procedure was the same as above.

As shown in Table 2, among 40 HIV-1+ sera, 9 (22.5%) show anti-p24, anti-gp120 and anti-RT antibodies, all being 1F7+. In 3 (7.5%) sera, two of three kinds of anti-HIV-1 antibodies are 1F7 Id+, and in 11 (27.5%) sera, only one kind of antibody is 1F7+. Altogether, 57.5% of HIV-1+ sera have at least one kind of anti-HIV-1 antibody which expresses 1F7 Id. These data confirm that it is common for the 1F7 Id clonotype to be shared by different anti-HIV-1 antibodies produced by the same individual.

TABLE 2

| Antibody | No. positive sera | 1F7Id | Percent 1F7 Id+ |
|---|---|---|---|
| Total anti-p24 | 30 | 18 | 60 |
| Total anti-gp120 | 36 | 16 | 44.4 |
| Total anti-RT | 15 | 12 | 80 |
| Total anti-tetanus toxoid | 39 | 0 | 0 |
| Anti-p24 + anti-gp120 + anti-RT | | 0 | 22.5 |
| Anti-p24 + anti-gp120 | | 1 | 2.5 |
| Anti-gp120 + anti-RT | | 1 | 2.5 |
| Anti-p24 + anti-RT | | 1 | 2.5 |
| Anti-p24 or anti-gp120 or anti-RT | | 11 | 27.5 |
| Total | | 23 | 57.5 |

EXAMPLE III

EVIDENCE THAT ANTI-HIV RESPONSES IN HIV+ INDIVIDUALS ARE OF RESTRICTED CLONAL ORIGIN

A. Determining Clonal Restriction of B-Cell Clones by Kappa/Lambda Light Chain Analysis

1. Methods

Purification of human serum antibodies was performed by coupling recombinant p24 (HIV-1 IIIB) (Pharmacia Genetic Engineering, La Jolla, Calif.) and recombinant gp120(SF-2) (Chiron Corporation, Emeryville, Calif.) to CNBr-activated Sepharose 4B (Pharmacia LKB, Biotechnology AB, Uppsala, Sweden). According to the manufacturer, IgG from HIV+ sera (North American Biological, Inc., Miami, Fla.) was purified on protein G sepharose. The Ig fraction was passed over affinity columns at 5 ml/hour. After washing, the column was eluted using 0.1 M glycine buffer (pH 2.5) with 0.01 M PBS (pH 7.0). The antibodies were dialyzed and concentrated for further use.

Detection of antibody light chain isotypes in normal (San Diego Regional Blood Bank, San Diego, Calif.) and unfractionated HIV+ human sera (North American Biological, Inc., Miami, Fla.) was performed by coating microtiter plates with goat anti-human IgG (TAGO, Inc., Burlingame, Calif.) at 100 µl/well of 1 µg/ml in 0.05 M bicarbonate buffer (pH 9.6) overnight at 4° C. and blocked with 2% BSA for three hours at room temperature. Sera was diluted 1:20,000 in 0.01 M PBS containing 0.1% Tween 20 (PBS-T) and incubated for two hours at room temperature. After washing three times with PBS-T, 100 µl of peroxidase conjugated goat anti-human kappa or lambda antibody (TAGO, Inc., Burlingame, Calif.) diluted 1:4,000 and 1:3,500, respectively, were added and incubated for 1.5 hours at room temperature. After washing, bound antibodies were visualized using O-phenylenediamine (OPD) (Sigma Chemical, St. Louis) and reaction was stopped with 3N $H_2SO_4$. Optical density (OD) was read at an absorbance of 490 nm (Molecular Devices Corporation, Menlo Park, Calif.). The kappa/lambda ratio was calculated according to the equation: ratio=OD of kappa/OD of lambda.

Detection of antibody light chain isotypes of purified anti-HIV antibodies was performed by coating microtiter plates with 5 µg, 2 µg or 1 µg of each recombinant gp120 (SF-2), gp120 (IIIB), p24, or RT (IIIB) in 0.05 M bicarbonate buffer (pH 9.6) overnight at 4° C., then blocked with 2% BSA for three hours at room temperature. Human sera diluted 1:100 in PBS-T were added and incubated for two hours at room temperature. Subsequent procedures were the same as described above.

Detection of light chain isotypes of anti-id 1F7 were performed by coating microtiter plates with 100 µl/well of 5 µg/ml of 1F7 in bicarbonate buffer overnight at 4° C., then blocked with 2% BSA for three hours at room temperature. 100 µl diluted human sera or human antibodies purified by HIV-1 antigen affinity chromatography were added and incubated for two hours at room temperature. Subsequent steps are the same as described above.

2. Results

In human sera, polyclonal immunoglobin usually consists of near equal amounts of kappa and lambda light chains. Over-representation of either light chain isotype is characteristic of monoclonal or oligoclonal antibody populations, as described in Müller et al., *J Immun* 147, 933 (1991). Forty randomly selected sera from HIV-1 infected individuals and forty normal sera were assayed by ELISA for binding to light chain isotype specific antisera as described above. When the kappa/lambda ratio was calculated none of the unfractionated HIV+ sera showed evidence of a monoclonal gammopathy.

Figure 5:
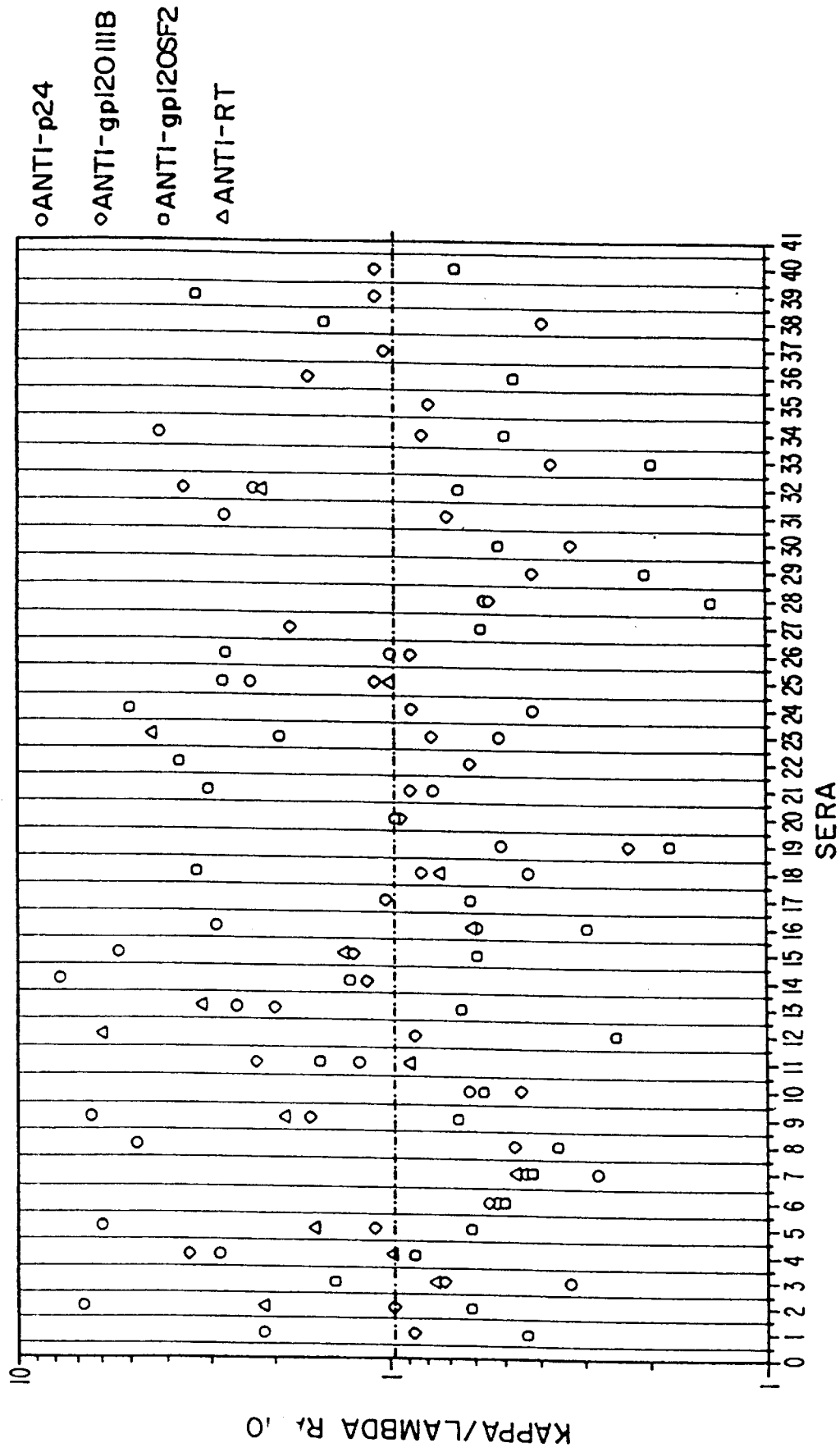
FIG. 5 shows the kappa/lambda ratio of anti-HIV antibodies, with sample number plotted along the y-axis and the ratio of various antibodies in each patient plotted along the x-axis.

The same kappa/lambda ratio analysis was then performed with antibodies derived from sera of forty different seropositive individuals specific for four different HIV-1 antigens. Antibodies to p24(IIIB), gp120 (2SF), gp120 (IIIB) and RT(IIIB) were captured by the corresponding insolubilized antigens. In contrast to the equivalent light chain isotype representation in total Ig, the showed either preferential kappa or lambda usage as represented in FIG. 5. FIG. 5 shows the kappa/lambda ratio for each patient was calculated as described above and plotted on the y-axis. 90% of the HIV+ sera had a skewed kappa/lambda ratio, demonstrating that oligoclonal or monoclonal anti-HIV antibodies are common in the sera of HIV+ individuals.

Figure 6A:
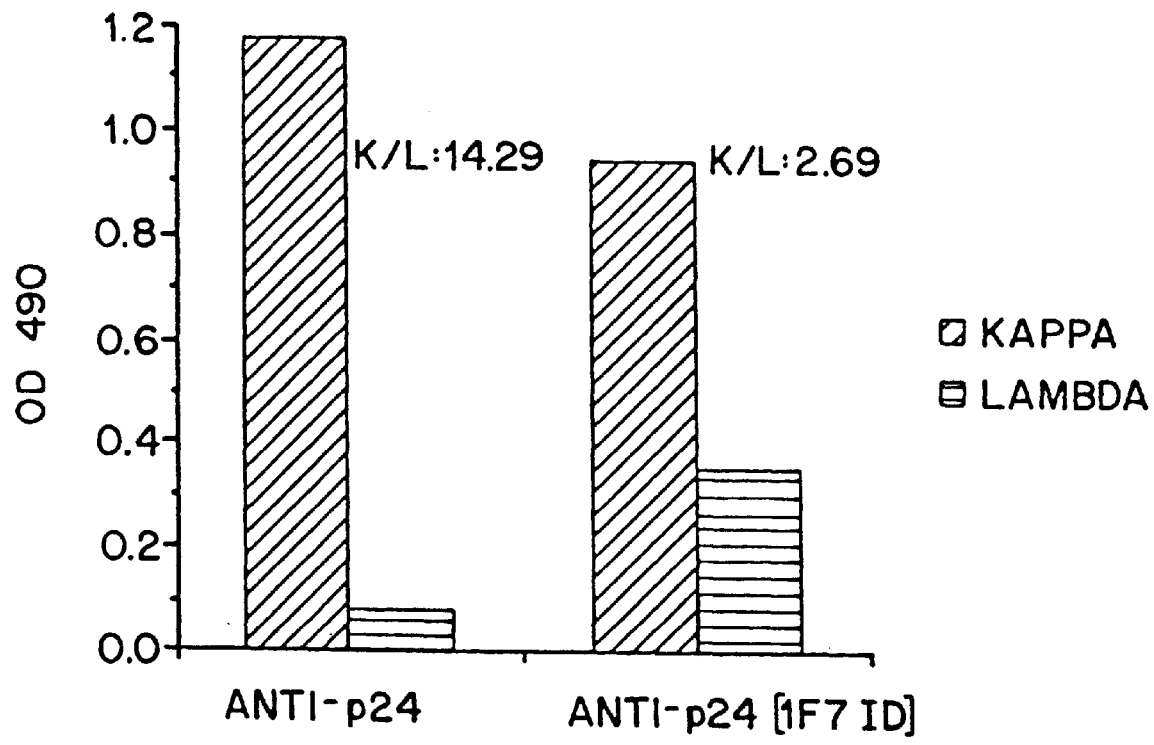
FIG. 6 shows the kappa/lambda ratio of affinity purified anti-p24 antibodies captured by p24 ELISA or 1F7 ELISA for patient 3-P14 (6a) and patient 3-P49 (6b).
Figure 6B:
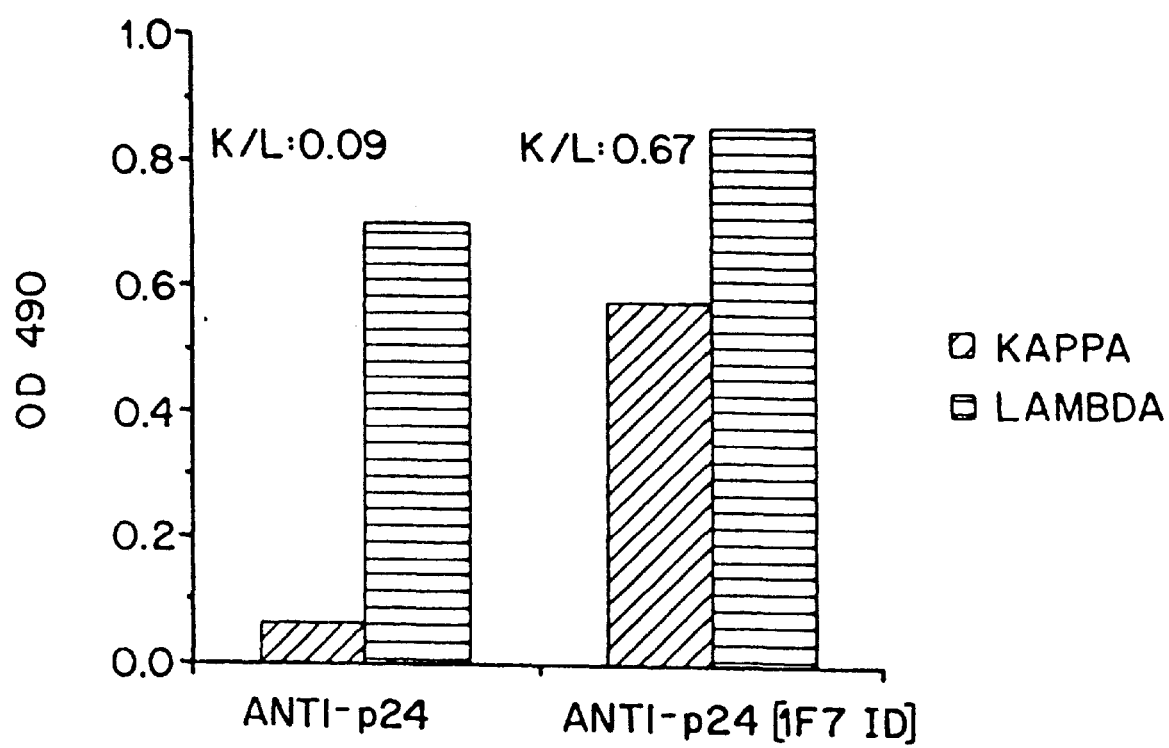
Figure 8A:
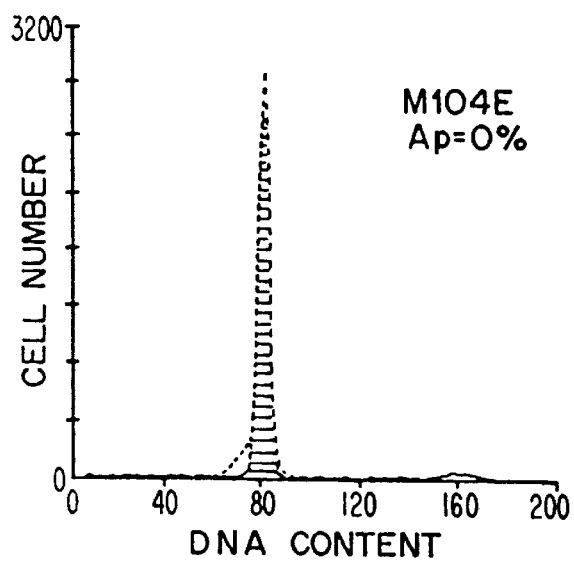
FIG. 8 shows histograms of DNA content on HIV− (8A and 8C) and HIV+ (8B and 8D) donor PBMC cells cultured with 1F7 or a control antibody.
Figure 8B:
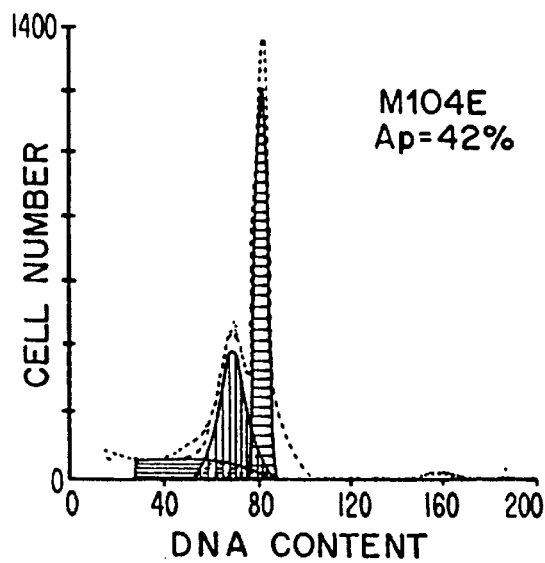
Figure 8C:
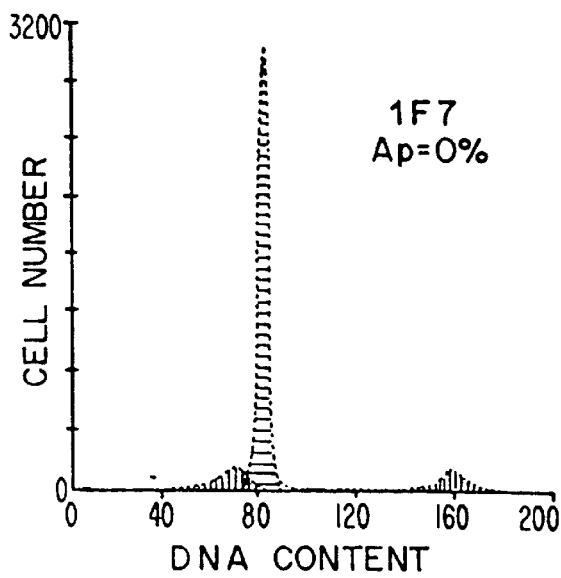
Figure 8D:
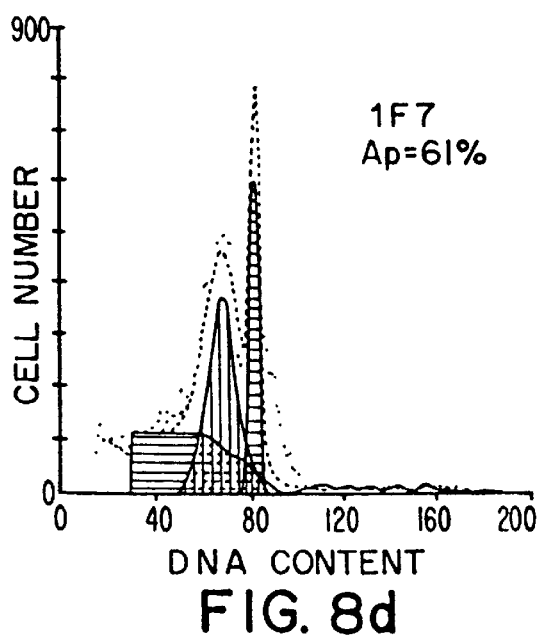

Subsequently, plates were coated with the 1F7 antibody and sera from HIV+ individuals added and reacted with either anti-kappa or anti-lambda antisera. Kappa and lambda light isotypes were both detected on 1F7 captured antibodies. To test whether 1F7 is associated with restricted anti-HIV antibodies, anti-p24 antibodies from different sera were purified by affinity chromatography as described in Example I. Both purified antibodies were then allowed to bind to p24 and 1F7 coated plates and the ratio of kappa to lambda calculated. As shown in FIG. 6a, ten times more kappa reactivity than lambda was found when assayed on p24 plates. The kappa/lambda ratios was significantly less skewed when assayed on 1F7 coated plates. This was also demonstrated for FIG. 6b, using sera from a second HIV+ individual. Collectively, this data demonstrated that anti-p24 responses consist of two populations of antibodies: one being clonally restricted and the other polyclonal.

B. Determining Clonal Restriction of B-cell Clones by Isoelectric Focusing

1. Method

Isoelectric focusing was performed using precast pH 3–10 gel according to the manufacturer (Novex, Novel Experimental Technology, San Diego, Calif.). The Novex system utilized a cathode buffer composed of 0.29% (w/v) arginine and 0.35% (w/v) lysine whereas the anode buffer consists of 0.47% (w/v) of phosphoric acid (85%). Anti-p 24 and gp120 (SF-2) antibodies purified by affinity chromatography were adjusted to a final protein concentration of approximately 100 µg/ml with sample buffer provided by Novex, 20 µl were applied to the gel. The Novex model 3540 power supply was programmed to produce three phases of constant voltage (i.e. 100 v for one hour followed by 200 v for one hour and, finally, 500 v for thirty minutes). The run time was for a total of 2.5 hours. The current per gel was set at a maximum of 8 mA. Visualization of isoelectric focusing separated proteins was by silver staining (Bio-Rad Laboratories, Richmond, Calif.).

2. Procedure

Figure 7:
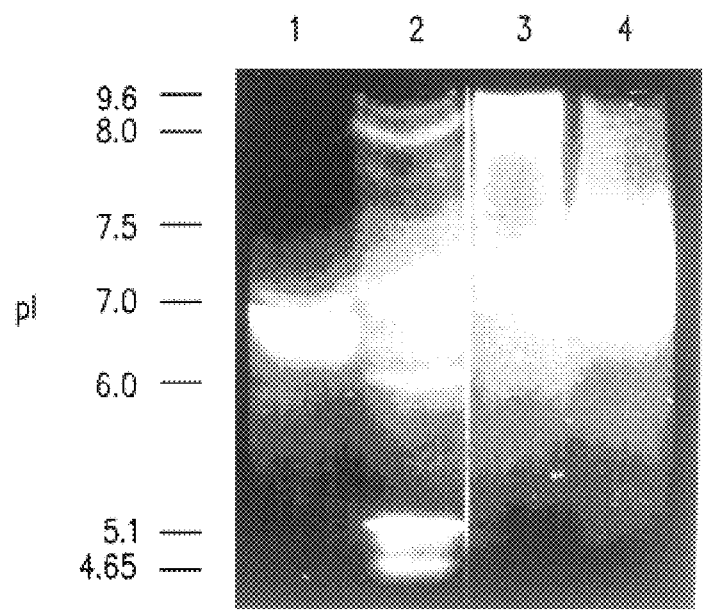
FIG. 7 shows the IEF pattern of purified anti-p24 and anti-gp120 antibodies.

To further demonstrate restricted character of anti-HIV antibody responses, the anti-p24 anti-gp120 antibodies with biased light chain isotypes were purified on affinity chromatography and submitted to isoelectric focusing. As seen in FIG. 7, anti-p24 and anti-gp120 antibodies show IEF bands typical for oligoclonal or monoclonal antibodies. The anti-p24 antibodies contains two IEF restricted banding clusters one at pH 8.5 to 9.6, and the other at pH 7.2 to 7.4. The anti-gp120 antibody shows one cluster at pH 7.0 to 7.5.

C. Determining Clonal Restriction of B-cell Clones by Immunoblot Analysis of Variable Region Diversity

1. Method of identifying $V_K$ and $V_H$

Immunodominant portions of the first framework region of Ig heavy and light chains were used for the creation of anti-peptide antisera that are specific for the $V_k$ and $V_H$ gene families according to the methods of Silverman et al., (*Arthritis and Rheumatology* 33,1347 (1990), *Journal of Immunological Methods* 95, 249 (1986), *Journal of Clinical Investigations* 88, 911 (1991)), all of which are herein incorporated by reference. Antisera were also used that identify first domains of heavy and light chain constant regions. Briefly, peptides were conjugated by their carboxyl-terminal cysteine to the carrier, keyhole limpet hemocyanin, prior to immunization of rabbits. To demonstrate the binding specificity of the peptide-induced reagents, Western immunoblot analyses were performed with 4 µg/lane of Ig proteins.

2. Procedure

Antibodies were affinity purified on p24 and gp120 immunoabsorbent columns respectively and used to analyze their variable region expression. The kappa/lambda analysis was performed on the sera used for purification, taken from four HIV+ patients, identified as 3-P14, 3-P49, P14, and P15. Ig chains were electrophoretically separated prior to transfer to membranes that were then probed with anti-peptide antibodies specific for Ig constant or variable region sequences. For each patient the total unfractionated IgG is compared to the affinity purified antibodies to HIV-1 gp120 and p24, and these compared to the monoclonal IgM proteins KAS ($V_{H1}$–$V_{K3}$) and HER ($V_{H3}$–$V_{K3}$) which serve as controls for subgroup specificity. The replicate panels were tested with antiserum specific for first framework sequences specific for the four $V_K$ families, and the major $V_H$ families, $V_{h1}$, $V_{H4}$ and $V_{H3}$. These families represent the overwhelming majority of circulating Ig and B cells in normal adults according to Berman et al., *Embo. J* 7, 727 (1988), Logtenberg et al. *Int. Immunol.* 1, 362 (1989), Guigou et al. *Mol. Immunol.* 27, 935 (1990), and Zouali et al. *J. Immunol* 146, 2855 (1991). The antiserum to Ig constant regions ($C_H$, $C_K$ and $C\lambda$) are used as controls. Immunoblots reveal that unfractionated IgG from normal controls and the four HIV-1 infected individuals contain subpopulations from all of these V region families. In contrast, the anti-p24 antibodies are all depleted of $V_{H3}$ derived H chains and enriched for VH1 derived H chains. Only one individual (3-P49) also had enrichment of anti-p 24 antibodies from the VH4 family. Anti-gp120 antibodies were also studied in three of these individuals (3-P14, 3-P49, P14). One of these individuals (p14) also had enrichment in $V_{H1}$ derived H chains and depleted in $V_{H4}$ and $V_{H3}$ H chains, while a second individual (3-P14) was found to have anti-gp120 antibodies with enrichment of $V_{H1}$ and $V_{H4}$ H chains, with depletion in $V_{H3}$ derived H chains. Patient 3-p49 also has $V_{H3}$ depleted in anti-gp120 antibodies. Analysis of the L chains revealed that both lambda and kappa L chains are used, but no consistent pattern of $V_k$ family usage was detected. The biased light chain isotype expression of anti-p24 antibodies from four selected sera was confirmed in Western blots using $V_K$ family specific antisera. Three out of four antibodies showed enrichment for $V_{KII}$ and depletion in lambda activity. The data on V gene family utilization and isotype expression are compiled in TABLES 3 and 4. The kappa/lambda and 1F7 ratios are determined by ELISA as described in Example 1 above. The 1F7 binding is determined by goat antimouse IgM-HRPO, and substrate and O.D. measured at 490 nm. Subgroup analysis wee performed with replicate immunoblots of isolated H and L chains using variable region family specific, anti-peptide antibodies as described above. Relative loading of H chains and L chains were demonstrated with antisera to gamma and Ck constant regions determinants respectively.

The results shown in TABLES 3 and 4 indicate clonal restriction in anti-HIV antibodies and are in agreement with the results obtained by IEF on purified anti-p24 and anti-gp120 antibodies.

TABLE 3

Immunoblot VH reactivity of affinity purified anti-HIV antibodies

| | SUBGROUP ANALYSIS | | | | | |
|---|---|---|---|---|---|---|
| | Gamma | VH1 | VH3 | VH4 | K/λ | 1F7+ |
| Anti-p24 | | | | | | |
| 3-p14 | +++ | ++++ | – | – | 14.29 | 1.593 |
| 3-p49 | ++ | ++ | – | +++ | 0.09 | 0.235 |
| p14 | ++ | ++ | – | – | 5.96 | 1.750 |
| p15 | +++ | ++++ | + | + | 2.86 | 0.786 |
| Anti-qp120 | | | | | | |
| 3-p14 | ++++ | +++ | – | ++++ | 0.25 | 0.568 |
| 3-p49 | ++++ | ++++ | +++ | ++++ | 0.62 | – |
| p14 | ++++ | ++++ | + | +++ | 0.61 | 1.043 |
| p15 | N.D. | N.D. | N.D. | N.D. | 0.87 | – |
| Anti-qp24 antibodies* | | | | | | |
| anti-p24(+) | ++ | +++ | + | + | | |
| anti-p24(–) | +++ | ++++ | ++++ | ++++ | | |

N.D. = Not Done
+, ++, +++, ++++, indicates relative band intensity
–, indicates not detected
*refers to affinity purified anti-p24 antibodies (eluate) compared to non-anti-p24 antibodies (flow through) from sera of HIV+ patients.

TABLE 4

Immunoblot VL reactivity of affinity purified anti-HIV antibodies

SUBGROUP ANALYSIS

|  | Ck | VkI | VkII | VKIII | VkIV | C1 |
|---|---|---|---|---|---|---|
| Anti-p24 |  |  |  |  |  |  |
| 3-p14 | ++++ | ++++ | ++++ | +++ | + | – |
| 3-p49 | ++ | – | – | ++ | + | +++ |
| p14 | + | + | +++ | + | ++ | – |
| p15 | +++ | ++ | +++ | +++ | ++ | + |
| Anti-qp120 |  |  |  |  |  |  |
| 3-p14 | ++++ | + | – | +++ | ++ | +++ |
| 3-p49 | ++++ | +++ | +++ | ++++ | ++++ | ++++ |
| p14 | ++++ | ++ | ++++ | +++ | + | ++++ |
| Anti-p24 antibodies* |  |  |  |  |  |  |
| anti-p24(+) | ++ | + | ++++ | ++ | ++++ | ND |
| anti-p24(−) | ++++ | ++++ | ++++ | ++++ | ++++ | ND |

*, see Table 3.

Collectively, the data on light isotype expression, IEF and V gene utilization provide strong evidence that the anti-HIV antibody responses in seropositive individuals are of restricted clonal origin.

EXAMPLE IV

Correlation of Presence of 1F7 Idiotope with Various HIV-related Disorders

A comparison of 1F7 idiotope expression in sera from various HIV infected and noninfected patients was conducted. The amount of circulating 1F7 positive immunoglobulin was measured in the following groups: seropositive B cell lymphoma patients, asymptomatic seropositive individuals, symptomatic seropositive patients (ARC and AIDS), and seronegative individuals including seronegative lymphoma patients.

A. MATERIAL AND METHODS

1. Sera

Sera from B cell lymphoma patients without HIV-1 infection were provided by San Diego Regional Cancer Center. Sera from HIV-1 virus infected patients, AIDS, ARC, and HIV-1 related lymphoma were provided from the AIDS study group of San Francisco General Hospital. Sera from 28 HIV-1 infected asymptomatic individuals and ARC/AIDS patients were provided by the Southwest Foundation for Biomedical Research, San Antonio, Tex. HIV seronegative and seropositive sera were purchased at the local blood bank.

2. Production of Mouse Monoclonal Anti-Idiotypic Antibody 1F7

Splenic cells from BALB/c mice immunized with human polyclonal anti-HIV-1 IgG were fused with Sp2/0 cells according to standard protocols as described in Example I above. Antibodies binding to HIVIG were detected using p24 and gp120 (IIIB) capture ELISA. One hybridoma (1F7, IgM), which bound to antibodies captured by HIV-1 antigens, not to IVIG and IVIG captured by non-HIV antigens, was subcloned and grown as ascites in BALB/c mice. Ascites fluid was purified on goat anti-mouse IgM Sepharose 4B column (Pharmacia LKB, Biotechnology AB, Uppsala, Sweden).

3. ELISA to Detect 1F7 on Human IgG and IgM

Microtiter plates were coated with 100 ng/well goat anti-mouse IgM at 4° C. overnight and blocked with 2% BSA. 100 ng 1F7 was added to each well and incubated at room temperature for 2 hours. After washing, 1:1000 diluted HIV-1+ or HIV-1− human sera was added to each well and incubated for another 2 hours. Subsequently, either peroxidase conjugated goat anti-human IgG (1:6000, Fisher Biotech, Pittsburgh, Pa.) or peroxidase conjugated goat anti-human IgM (1:1000) were added for 1.5 hours. Bound 1F7+ antibodies were visualized using o-phenylenediamine OPD (Sigma Chemical, St. Louis, Mo.) and the reaction was stopped with 3 N $H_2SO_4$. Absorbance was read spectrophotometrically at 490 nm (Molecular Devices Corporation, Menlo Park, Calif.).

4. Statistical Methods

Statistical analysis to calculate the significance of differences between groups was undertaken using a t-test for unpaired variables. For calculation of predictive values, sensitivity and specificity, the Newman-Keuls Multiple Comparison Test was used.

B. RESULTS

The expression of the 1F7 idiotope in sera from HIV infected and noninfected patients is shown below in TABLE 5. Data is indicated as the mean of the log of the optical density at 490 nm ×1000, together with the calculated standard deviation in each patient group. It can be seen that the highest correlation occurs for HIV+ related lymphoma.

It was also established that the elevation of 1F7-Id in polyclonal antibodies in HIV+ lymphoma patients was not due to a variation of total Ig. Total immunoglobin in sera from randomly selected patients with ARC/AIDS or AIDS related non-Hodgkin B cell lymphoma (AIDS-NHL) was determined by standard procedures in the clinical reference laboratory of the San Francisco General Hospital. Total Ig in 10 sera from the ARC/AIDS cohort (that is, group of statistically equivalent individuals) and in 10 sera from the AIDS lymphoma patient cohort was found to be in the same range. In addition, it was established that the 1F7 marker was more than a marker for the longevity of the disease, since the levels of 1F7-Id expression in sera were not found to be correlated with the decrease of the CD4 cell count. CD4 cell count considered to be a parameter for disease progression from asymptomatic stages of HIV-1 infection to AIDS. A survey of 1F7-Id expression in sera from 10 HIV+ individuals with a CD4 cell count higher than 400 cells/$mm^3$, sera from 10 patients with a CD4 cell count between 200 and 400 cells/$mm^3$, and sera from 8 patients with a CD4 cell count lower than 200 cells/$mm^3$ revealed no significant differences in titers of antibodies expressing 1F7 idiotope.

TABLE 5

EXPRESSION OF 1F7 IDIOTOPE ON IqG AND IgM IN HIV-1 + AND HIV-1 − SERA

| Group | # of sera | IgG | IgM |
|---|---|---|---|
| HIV + Lymph | 44 | 2.60 +/− 0.50 | 1.77 +/− 0.61 |
| ARC | 76 | 1.73 +/− 0.59 | 1.15 +/− 0.48 |

TABLE 5-continued

EXPRESSION OF 1F7 IDIOTOPE ON IqG AND IgM
IN HIV-1 + AND HIV-1 − SERA

| Group | # of sera | IgG | IgM |
| --- | --- | --- | --- |
| AIDS | 75 | 1.56 +/− 0.64 | 1.25 +/− 0.41 |
| Asymptomatic | 90 | 1.41 +/− 0.65 | 1.32 +/− 0.52 |
| HIV − | 60 | 1.10 +/− 0.41 | 0.89 +/− 0.32 |
| HIV − Lymph | 20 | 0.82 +/− 0.38 | 0.71 +/− 0.04 |

It can be seen that the highest correlation for the expression of 1F7 is obtained for HIV+ lymphoma.

Therefore, a statistical analysis of 1F7+ idiotope expression in sera from patients with HIV-1 related lymphoma was performed. 1F7 idiotope expression in HIV-1 related lymphoma was compared to all other HIV+ groups (pooled). This can be seen in TABLE 6 below. 1F7 idiotope expression on IgG antibodies is highly specific (95%) and highly sensitive (90%) in patients with HIV related lymphoma. The positive predictive value for lymphoma in HIV-1 infected individuals was calculated to be 0.755.

TABLE 6

PREDICTIVE VALUE, SENSITIVITY AND SPECIFICITY
OF 1F7 ID EXPRESSION IN HIV-1 RELATED LYMPHOMA

| Statistical Parameter | 1F7 + Id on IgG Ab | 1F7 + Id on IgM Ab |
| --- | --- | --- |
| Pos. Predictive Value | 0.755 | 0.295 |
| Neg. Predictive Value | 0.984 | 0.935 |
| Sensitivity | 90.9% | 70.5% |
| Specificity | 95.0% | 71.6% |

In the survey described above and shown in TABLE 6 there is strong evidence that the described HIV-1 associated idiotope 1F7 serves as a marker for HIV-1 related B-cell lymphoma. 93% of HIV-1 infected patients with lymphoma tested positive for 1F7 expression. Significantly lower levels of 1F7 idiotope were detected in HIV-1 infected patients without lymphoma.

According to the calculated statistical parameters as shown in TABLE 6, high levels of 1F7 Id expression can predict AIDS associated lymphoma in 75% of cases. This strongly suggests that the 1F7 idiotope can be used as a disease marker.

EXAMPLE V

ENHANCEMENT OF APOPTOSIS IN HIV+ PATIENTS BY 1F7

A. MATERIALS AND METHODS 1. 1F7 Stimulation of PBML Cell Culture

Blood from 20 HIV sero-positive donors was obtained from the University of California San Francisco hospital from Michael McGrath. Blood from 8 HIV sero-negative donors were collected from laboratory workers. Whole blood from donors was collected, and clotting prevented by treatment with citrate according to methods known in the art. Plasma was collected after centrifuging at low speed and stored frozen until anti-1 F7 levels were tested. Peripheral blood mononuclear lymphocytes (PBML) were isolated from whole blood by centrifugation on "Lymphoprep" (Nycomed, Norway), according to manufacture's suggestions. PBMLs were collected from the top of the Hypaque cushion, and washed free of human serum by repeated spins in "Growth Medium" (RPMI-1640 plus 10% (V/V) fetal calf serum (Hyclone, USA) including 1 mM L-Glutamine, 1 mM Sodium-Pyrovate, $\frac{1}{100}$ non-essential amino acids (all GIBCO), 50 mM HEPES (SIGMA), pH 7.4). The cells were plated out at a concentration of $2.5 \times 10^6$/ml in 2 ml/well of a 24 well tissue culture plate (Costar). Cells were cultivated in Growth Medium in the presence of 5 µg/ml mouse IgM antibody, either MOPC-104E (Sigma, St. Louis, Mo.) or TEPC 183 (isotype control antibody, Sigma, St. Louis, Mo.) or 1F7 (isolated from hybridoma supernatant or ascites fluid, as described above). Cells were harvested after cultivation for 1, 3, 7 or 10 days for determination of levels of apoptosis.

2. CD4+ and CD8+ depletion

CD4+ or CD8+ cell free fractions were generated by negative selection from the PBMLs of HIV sero-positive donors. These donors were arbitrarily selected among donors with CD4+ cell counts above 500. Magnetic beads, commercially available as Dynabeads (DYNAL), labeled with either anti-CD4 antibodies or anti-CD 8, were incubated with PBMLs at a ratio of 3:1, beads to target cells, at 4° C. for 30 minutes under gentle rotation end over end. Beads, and cells bound to beads were isolated by means of attraction to a strong magnet according to the manufacturer's direction. The remaining cells were collected. Extraction success was determined by flow cytometry analysis of the remaining population. Extraction was always better than 95%. This population was subsequently cultivated and subjected to apoptosis determination.

3. Double Staining with FITC and PI

Cells were harvested from culture and stained with fluorescein (FITC)-conjugated antibodies to CD4 and CD8 (Gentrak, Plymouth Meeting, Pa). FITC-conjugated murine isotype (Gentrak) was used as a staining control. After staining, the cells were resuspended in propidium iodide (20 µg/ml in 0.112% sodium citrate) (Sigma, St. Louis, Mo.) and incubated for 30 minutes at room temperature prior to cytometric analysis.

Flow cytometric analysis was carried out on a FACScan (Becton Dickinson, San Jose, Calif.). Two-parameter cytograms of red fluorescence (DNA content) versus green fluorescence (FITC) were generated to determine the percentage of cells that were CD4 or CD8 positive.

4. Quantitation of DNA Degradation (Apoptosis) by Propidium Iodide (PI)

Cells were harvested from culture and fixed with 70% ETOH for a minimum of 3 hours. After 2 washes cells were resuspended in PI (50 µg/ml PI, 180 U/ml RNase in PBS) (Sigma, St. Louis, Mo.) and incubated for 30 minutes at room temperature prior to flow cytometric analysis.

Flow cytometry was performed on an Epics I (Coulter Electronics, Hialeah, Fla.) using doublet discrimination in the measurement of DNA followed by a MULTICYCLE (Phoenix Flow Systems, San Diego, Calif.) software program. The percentage of DNA to the left of the $G_0/G_1$ peak was taken to represent DNA lost from the original 2 N quantity as a result of apoptotic degradation.

B. RESULTS

1F7-Induced Apoptosis of PBMLs from HIV+ donors

Figure 9:
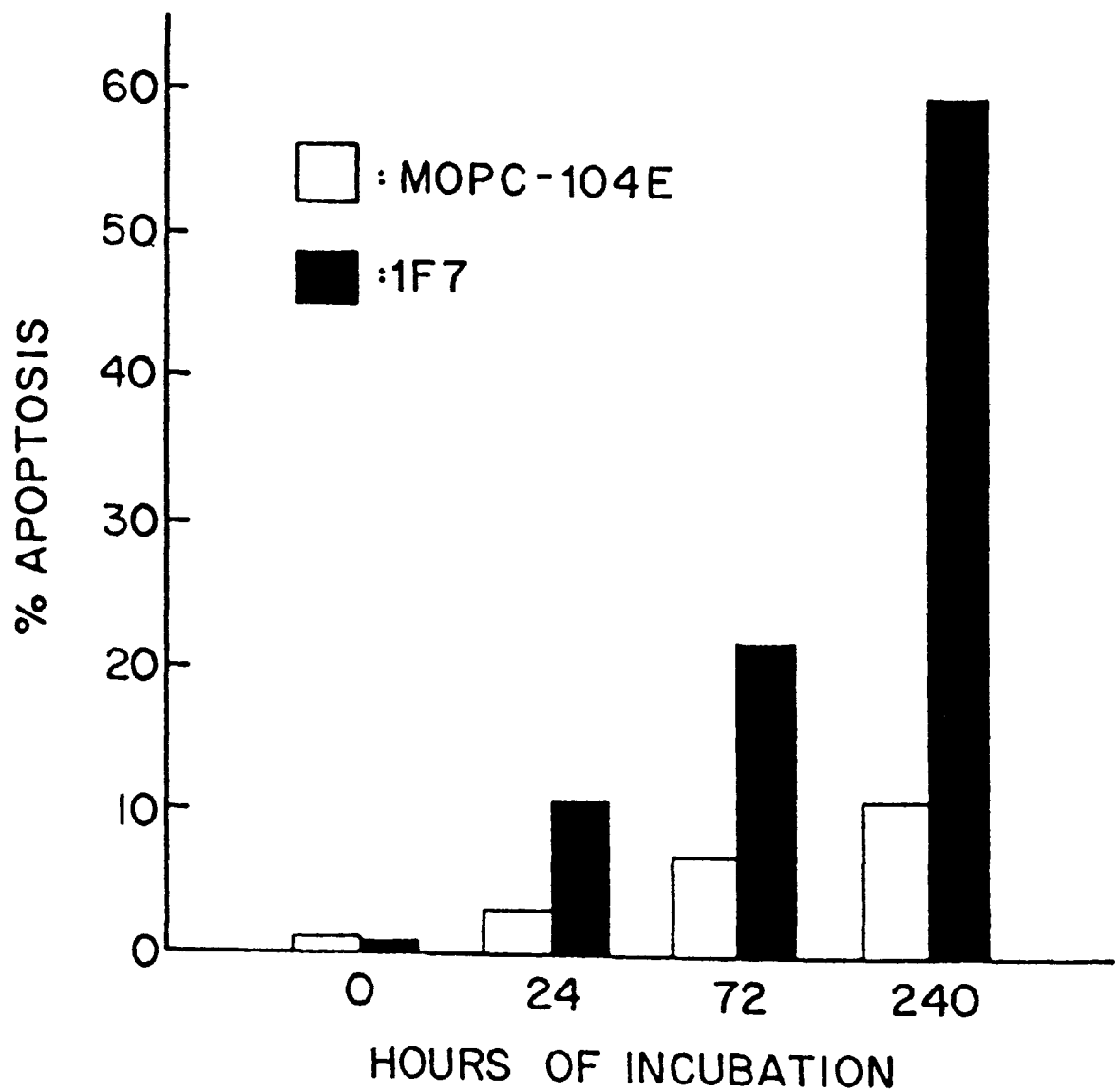
FIG. 9 shows 1F7 induced apoptosis on PBML cell cultures from HIV+ donors compared with apoptosis induced with a control antibody.
Figure 10:
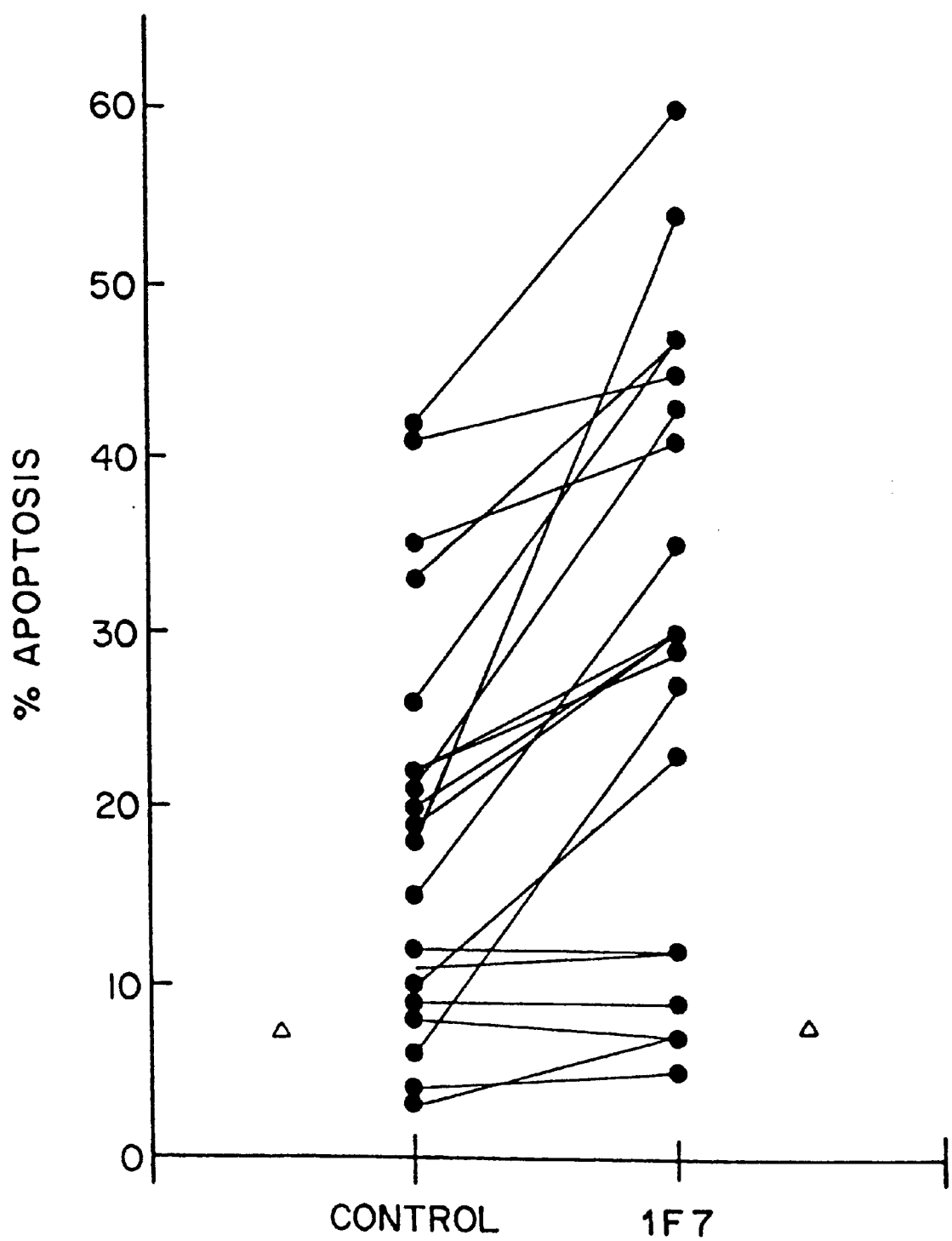
FIG. 10 shows the comparison of spontaneous apoptosis with 1F7 induced apoptosis on PBML cell cultures from HIV+ donors.

A typical example of PBMC (peripheral blood mononuclear cells) from an HIV seropositive donor undergoing 1F7-induced apoptosis is shown in FIG. 8 (panel B and D) after an in vitro incubation of PBMC for 7 days. FIG. 8 is a histogram of DNA content on HIV-(histogram A and C) and HIV+ (histogram B and D) donor PBMC after 7 day culture with either mouse IgM (MOPC-30 104E) or 1F7. Data was generated after fixation and staining with PI as described above. Histograms A and C show no apoptosis in the PBMC of HIV− healthy control donor as measured by the amount of degraded DNA. The onset of 1F7-induced apoptosis in PBMC derived from this patient could be observed after 24 hours (FIG. 9). The level of spontaneous apoptosis was compared to 1F7 induced apoptosis by PBMCs from 20 different HIV+ donors after 7 days of culture (see FIG. 10). 1F7 significantly increased the level of apoptosis for 16 donors (>3% increase), whereas cells from 4 donors were not affected. The average number of spontaneous to 1F7 induced cells in apoptosis is 19% and 32% respectively. Apoptosis of PBMLs from 8 HIV− donors were unaffected by 1F7. There was no significant correlation between spontaneous apoptosis levels and degree to which 1F7 induced apoptosis.

2. 1F7 induced apoptosis in PBMLs depleted of CD4+ or CD8+ cells

In order to determine if the observed apoptosis induced with 1F7 was associated with cells of a particular phenotype, PBMLs from a HIV+ donor were separated into a CD4− population and a CD8−population by negative selection. The effect of 1F7 on these populations were compared to a preparation of unseparated PBMLs from the same donor (see Table 7). PBMLs from an HIV sero-positive donor were divided into three pools: One remained complete, the second was depleted of CD4+cells and the third was depleted of CD8+cells. Subsequently each pool was cultivated for 3 or 7 days with either 5 μg/ml of a control antibody, MOPC-104E (Sigma, St. Louis, Mo.), or 5 μg/ml 1F7 at what point the level of apoptosis was determined by flow cytometry. Table 7 below shows that 1F7 induced approximately 4× control levels of apoptosis in the CD4− population early after start of culture. This in contrast to 1F7 induced apoptosis in the CD8−population was less severe, and slower, approximately 2 times less than control levels.

TABLE 7

| Culture Conditions | | Percent Apoptosis | | |
| --- | --- | --- | --- | --- |
| | | Complete | CD4−/CD8+ | CD8−/CD4− |
| Day 3 | Control | 13 | 11 | 17 |
| | 1F7 | 16 | 41 | 17 |
| Day 7 | Control | 4 | 4 | 17 |
| | 1F7 | 5 | 5 | 29 |

In summary, it was found that the 1F7 antibody induced apoptosis in 16 of the 20 HIV+ samples, and none of the HIV− control samples. Apoptotic cells appear in the AO regions with a DNA below that of the G0/G1 cells. Flow cytometric analysis and lymphocyte subset depletion experiments demonstrated that cells undergoing apoptosis were T cell subset CD8+ cells.

EXAMPLE VI

1F7 INFLUENCE ON T CELL-MEDIATED CYTOTOXICITY

In addition to the enhancement of apoptosis in HIV+ patients by 1F7, experiments indicate that 1F7 reduces T-cell mediated cytotoxicity. Because CD8+ cytotoxic T-lymphocytes (CTL) are known to circulate in HIV-1 infected individuals, a reduction in CTL activity in response to 1F7 indicates that 1F7 is capable of influencing the composition of T cells by reducing the number of CD8+ cells. The following experiments were performed according to the methods described in Grant et al., *AIDS* 6, 1085 (1992), which is herein incorporated by reference.

In one experiment, the addition of 1F7 at the start of cell culture reduced T cell-mediated cytotoxicity in IL-2 stimulated PBMC cultures, as measured by anti-CD3 mediated lysis of P815 cells. The experiment was performed as follows. Peripheral blood lymphocytes from 3 HIV+ individuals (same source as Example V) were cultured at $1 \times 10^6$/ml in media plus 1 μg/ml of either 1F7 or an IgM isotype control MOPC-104E (Sigma,). After 3 days, recombinant IL-2 (Genzyme, Cambridge, Mass.) was added at 5 units/ml. After 4 days in IL-2, the lymphocytes were tested for total CTL activity by redirected lysis of anti-CD3 coated P815 cells according to Grant et al., supra. Anti-CD8 coated P815 cells were used as a negative control and were not killed. It was found that cells cultured with 1F7 experienced a reduction in percent CTL-mediated lysis when compared with the control of between approximately 35 percent to approximately 20 percent to approximately 50 percent of the control, depending on the effector to target ratio, which was varied from 25:1 to 12.5:1 to 6.25:1. The CTL-mediated lysis assays were performed according to Grant et al., *supra*, at page 1087.

In a second set of experiments, incubation of CTL-derived from HIV+ individuals with 1F7 immediately before standard $^{51}$Cr release assays (Grant et al., *supra*, at page 1087) also reduced lysis of specific targets. The specific targets in this case were EBV (Epstein-Barr virus)-transformed B cells infected with various recombinant vaccinia/HIV constructs, as described in detail in Grant et al., *supra*, at page 1087. Anti-HIV CTL were generated by stimulating peripheral blood lymphocytes from an HIV-1 infected individual with autologous PHA-activated lymphocytes. After 3 days of stimulation, recombinant IL-2 (Genzyme, Cambridge, Mass.) was added at 5 units/ml for an additional 7 days before cells were tested. Autologous EBV-transformed B cells infected at a MOI of 15 overnight with vaccinia recombinants described above expressed either individual HIV proteins or b-galactosidase as a control. Immediately before asays $1 \times 10^6$ effector cells were incubated for 45 minutes with 1 μg/ml of either 1F7 or MOPC-104E (Sigma, St. Louis, Mo.). After incubation, effector cells were washed twice and tested for cytolysis of autologous EBV-transformed B cells infected at an MOI of 15 overnight with vaccinia recombinants expressing HIV gag, pol or env or E. coli β-galactosidase (lacZ) as a control. Cells incubated with 1F7 had a reduced percent specific lysis of approximately 30 percent of the control lysis depending on the effector: target ratio.

Although the invention has been described with reference to the presently-preferred embodiment, it should be understood that various modifications can be made without departing from the spirit of the invention. Accordingly, the invention is limited only by the following claims.

We claim:

1. A method of reducing T cell-mediated cytotoxicity in HIV+ sera comprising administering a sufficient amount of an anti-idiotypic monoclonal antibody or binding fragment thereof having specific reactivity with an idiotope specifically bound by monoclonal antibody 1 F7 produced by hybridoma ATCC Accession No. HB 11286, and which idiotope is common to at least three types of human anti-HIV-1-antibody of differing specificites, but not significantly reactive with idiotypes of human non-HIV-1 antibodies.

2. The method of claim 1 wherein the monoclonal antibody which is designated 1F7 is produced by hybridoma ATCC Accession No. HB11286.

3. The method of claim 1, wherein the idiotope is a clonotype of human polyclonal anti-HIV-1 antibodies.

* * * * *